US006995016B2

(12) United States Patent
Eudes et al.

(10) Patent No.: US 6,995,016 B2
(45) Date of Patent: Feb. 7, 2006

(54) PROCESS FOR INDUCING DIRECT SOMATIC EMBRYOGENESIS IN IMMATURE SCUTELLA CELLS OF POOIDEAE, AND RAPIDLY REGENERATING FERTILE PLANTS

(75) Inventors: Francois Andre Germain Eudes, Lethbridge (CA); Andre J. Laroche, Lethbridge (CA); Surya Narayan Acharya, Lethbridge (CA)

(73) Assignee: Her Majesty the Queen in right of Canada, as represented by the Minister of Agriculture and Agri-Food, Lethbridge (CA)

( * ) Notice: Subject to any disclaimer, the term of this patent is extended or adjusted under 35 U.S.C. 154(b) by 302 days.

(21) Appl. No.: 09/929,831

(22) Filed: Aug. 14, 2001

(65) Prior Publication Data

US 2002/0164798 A1 Nov. 7, 2002

Related U.S. Application Data

(63) Continuation-in-part of application No. 09/641,243, filed on Aug. 17, 2000, now abandoned.

(51) Int. Cl.
*C12N 15/82* (2006.01)

(52) U.S. Cl. .............................. 435/430.1; 435/430.1; 800/278

(58) Field of Classification Search ................ 435/424, 435/430.1

See application file for complete search history.

(56) References Cited

U.S. PATENT DOCUMENTS

| 4,666,844 A | | 5/1987 | Cheng ........................ 435/240 |
| 5,322,789 A | | 6/1994 | Genovesi et al. ......... 435/240.5 |
| 5,409,828 A | | 4/1995 | Frenkel et al. ............ 435/240.4 |
| 5,445,961 A | | 8/1995 | Genovesi et al. ......... 435/240.5 |
| 5,589,617 A | * | 12/1996 | Nehra et al. ................ 800/278 |
| 5,610,042 A | | 3/1997 | Chang et al. ............. 435/172.3 |
| 5,631,152 A | | 5/1997 | Fry et al. .................. 435/172.3 |
| 5,641,664 A | | 6/1997 | D'Halluin ................. 435/172.3 |
| 5,712,135 A | | 1/1998 | D'Halluin ................. 435/172.3 |
| 5,792,936 A | | 8/1998 | Dudits et al. ............... 800/230 |
| 5,874,265 A | | 2/1999 | Adams et al. ............ 435/172.3 |
| 5,981,842 A | | 11/1999 | Wu et al. .................... 800/298 |
| 6,071,746 A | | 6/2000 | Seabrook et al. ............ 435/429 |

FOREIGN PATENT DOCUMENTS

| CA | 1292959 | 10/1991 |
| EP | 0720 425 B1 | 2/1998 |
| WO | WO 99/04618 | 2/1999 |
| WO | WO 00/16610 | 3/2000 |

OTHER PUBLICATIONS

Denchev et al. Transgenic orchardgrass (*Dactylis glomerata*) plants by direct embryogenesis from microprojecticle bombarded leaf cells. 1997. Plant Cell Reports, 16: 813-819.*
Mariani et al. Changes in Surface Structure during Direct Somatic Embryogenesis in Rice Scutellum Observed by Scanning Electron Microscopy. 1998. Plant Prod. Sci. 1 (3) : 223-231.*
Jong et al. Somatic Embryogenesis and Plant Regeneration from Inflorescence Callus of *Zizania latifolia* Turcz. 1987. J. Plan Physiol. vol. 130, pp. 67-71.*
Sankhla et al. Influence of growth regulators on somatic embryogenesis, plantlet regeneration, and post-transplant survival of *Echinochloa frumentacea*. 1992. Plant Cell Reports 11: 368-371.*
Sudhersan et al. Occurrence of direct somatic embryogenesis on the sword leaf of in vitro plantlets of *Phoenix dactylifera* L. cultivar barhee. 1993. Current Science, vol. 65, No. 11, pp. 887-889.*
Dale. Embryoids from Cultured Immature Embryos of *Lolium multiflorum*. Z. Pflanzenphysiol. Bd. 100. S. 73-77. 1980.*
Dunstan et al. Further Studies on Plantlet Production From Cultured Tissues of *Sorghum bicolor*. Protoplasma 101, pp. 355-361, 1979.*
Dunstan et al. The Anatomy of Secondary Morphogenesis in Cultured Scutellum Tissues of *Sorghum bicolor*. Protoplasma 97 pp. 251-260, 1978.*
Mantell et al. Principles of Plant Biotechnology an Introduction to Genetic Engineering in Plants. Blackwell Scientific Publications, pp. 141-143, 1985.*

(Continued)

*Primary Examiner*—Anne Kubelik
*Assistant Examiner*—June Hwu
(74) *Attorney, Agent, or Firm*—Greenlee, Winner and Sullivan, P.C.

(57) ABSTRACT

A process is provided for inducing direct somatic embryogenesis in Pooideae and rapidly regenerating fertile plants by first culturing isolated immature scutella cells in culture medium comprising auxin, cytokinin and polyamine in amounts effective to cause direct formation of primary embryos without an intervening callus stage, at least until at least one primary embryo reaches the globular developmental stage, the auxin being present in greater proportion than cytokinin. A second step includes either a) culturing the primary embryos under conditions to regenerate plantlets, and culturing the primary embryos in regeneration medium; or b) culturing the primary embryos at the globular developmental stage and no longer than the coleoptilar stage in culture medium comprising auxin, cytokinin, and polyamine in amounts effective to cause induction of secondary embryo formation, at least until secondary embryogenesis is detected, the cytokinin being present in greater proportion than auxin, and culturing the secondary embryos under conditions to regenerate plantlets.

56 Claims, 3 Drawing Sheets

OTHER PUBLICATIONS

Sargent et al. The effect of exogenous polyamines on somatic embryogenesis and plant regeneration from *Sorghum bicolor* and *Saccharum spp.* Acta horticulturae, Aug. 1998. No. 461, pp. 451-458.*

Ahokas, H. (1989) Transfection of germinating barley seed electrophoretically with exogenous DNA. Theor. Appl. Genet. 77:469-472.

Ahloowalia, B.S. (1982) Plant regeneration from callus culture in wheat. Crop Sci. 22: 405-410.

Alber, T. and Kawasaki, G. (1982) Nucleotide sequence of the triose phosphate isomerase gene of *Saccharomyces cerevisiae*. Journal of Molecular and Applied Genetics 1: 419-434.

Antonelli, N.M. and Stadler, J. (1990) Genomic DNA can be used with cationic methods for highly efficient transformation of maize protoplasts. Theor. Appl. Genet. 80: 395-401.

Arteca, R. (1996) Plant Growth Substances: Principles and Applications. New York. Chapman & Hall.

Barcelo, P., Hagel C., Becker, D., Martin, A. and Lörz H. (1994) Transgenic cereal (tritordeum) plants obtained at high efficiency by microprojectile bombardment of inflorescene tissue. Plant Journal 5: 583-592.

Barro, F., Cannell, M.E., Lazzeri, P.A. and Barcelo, P. (1998) The influence of auxins on transformation of wheat and tritordeum and analysis of transgene integration patterns in transformants. Theor. Appl. Genet. 97: 684-695.

Becker, D., Brettschneider, R. and Lörz, H. (1994) Fertile transgenic wheat from microprojectile bombardment of scutellar tissue. Plant Journal 5:299-307.

Bevan, M.W., Flavell, R.B. and Chilton, M.D. (1983) A chimaeric antibiotic resistance gene as a selectable marker for plant cell transformation. Nature 304: 184-187.

Bhaskaran, S. and Smith, R.H. (1990) Regeneration in cereal tissue culture: a review. Crop Sci. 30(6):1328-1337.

Bregitzer, P., Dahleen, L.S. and Campbell, R.D. (1998) Enhancement of plant regeneration from embryogenic callus of commerical barley cultivars. Plant Cell Rep. 17: 941-945.

Burkhardt, P.K., Beyer, P., Wunn, J., Kloti, A., Armstrong, G.A., Schledz, M., Lintig, J. and Potrykus, I. (1997) Transgenic rice (*Oryza sativa*) endosperm expressing daffodil (*Narcissus pseudonarcissus* ) phytoene synthase accumulates phytoene, a key Intermediate of provitamin A biosynthesis. Plant J. 11: 1071-1078.

Carman, J.G. (1990) Embryogenic cells in plant tissue cultures: occurrence and behavior. In Vitro Cell Dev. Biol.: 26: 746-753.

Cho, M.J., Jiang, W.I. and Lemaux, P. (1998) Transformation of recalcitrant barley cultivars through improvement of regenerability and decreased albinism. Plant Science 138: 229-244.

Creissen, G., Smith, C., Francis, R., Reynolds, H. and Mullineaux, P. (1990) *Agrobacterium*—and microprojectile—mediated viral DNA into barley microspore derived cultures. Plant Cell Rep. 8: 680-683.

De La Fuente, J.M., Ramirez-Rodriguez, V., Cabrera-Ponce, J.L. and Herrera-Estrella. L. (1997) Aluminum tolerance in transgenic plants by alteration of citrate synthesis. Science 276: 1566-1568.

Depicker, A., Strachel, S., Dhaese, P., Zambryski, P. and Goodman, H.M. (1982) Nopaline synthase: transcript mapping and DNA sequence *Agrobacterium tumelaciens*. J. Mol. Appl. Genet. 1(6): 561-573.

Elliott, M.C., Moloney, M.M., Scott, N.W. and Slater, A. (1996) A way forward for tobacco—molecular farming. Biotech. and Biotechnol. Equip. 4: 59-66, (Abstract only).

Fischer, R., Drossard, J., Commandeur, U., Schillberg, S. and Emans, N. (1999) Towards molecular farming in the future: moving from diagnostic protein and antibody production in microbes to plants. Biotech. and Apol. Biochem. 30(2): 101-108.

Fromm, M.E., Taylor, L.P. and Walbot, V. (1986) Stable transformation of maize after gene transfer by electroporation. Nature 319: 791-793.

Gamborg, O.L., Miller, R.A. and Ojima, K. (1968) Nutrient requirements of suspension cultures of soybean root cells. Exp. Cell Res. 50:151-158.

George, E.F., Puttock, D.J.M. and George, H.L. (1987) Plant Culture Media vol. 1, Formulations and Uses. Exegetics Limited.

Gielen, J., De Beuckeleer, M., Seurinck, J., Deboeck, F. and De Greve, H. (1984) The complete nucleotide sequence of the TL-DNA of the *Agrobacterium tumefaciens* plasmid pTiAch5. EMBO J. Eur. Mol. Biol. Organ. 3(4):835-846.

Green C.E. (1982) Somatic embryogenesis and plant regeneration from the friable callus of *Zea mays*. In Plant Tissue Culture 1982: Proceedings, Fifth International Congress of Plant Tissue and Cell Culture. Fujiwara, A. Ed. Tokyo and Lake Yamanake, Japan, Jul. 11-16, pp. 107-108.

Gruber, Margaret Y. Crosby, William L. (1993) Vectors for Plant Transformation. Methods in Plant Molecular Biology and Biotechnology. Boca Raton, CRC Press. Chapter 7:89-119.

Hayashi, H., Alia., Mustardy, L., Deshnium, P., Ida, M. and Murata. N. (1997) Transformation of *Arabidopsis thaliana* with the codA gene for choline oxidase; accumulation of glycinebetaine and enhanced tolerance to salt and cold stress. Plant J. 12: 133-142.

Hemming, D. (1995) Molecular farming: using transgenic plants to produce novel proteins and other chemicals. AgBiotech News and Info. 7(1):19-29.

Jacobsen, J.V. and Close, T.J. (1991) Control of transient expression of chimaeric genes by gibberellic acid and abscisic acid in protoplasts prepared from mature barley aleurone layers. Plant Mol. Biol. 16: 713-724.

Jähne, A., Becker, D. and Lorz, H. (1995) Genetic engineering of cereal crop plants: a review. Euphytica 85: 35-44.

Jähne, A., Becker, D., Brettschneider, R., and Lörz, H. (1994) Regeneration of transgenic, microspore-derived, fertile barley. Theor. Appl. Genet. 89: 525-533.

Kaneko, T., Kuroda, H., Hirota, N., Kishinami, t., Kimura, N. and Ito, K. (1991) Two transformation systems of barley—electroporation and laser perforation. Barley Genetics VI:231-233.

Knudsen, S. and Müller, M. (1991) Transformation of the developing barley endosoerm by particle bombardment. Planta. 185: 330-336.

Lee, B.T., Murdoch, K., Topping, J., Jones, M.G.K. and Kreis, M. (1991) Transient expression of foreign genes introduced into barley endosperm protoplasts by PEG-mediated transfer or into endosperm tissue by microprojectile bombardment. Plant. Sci. 78: 237-246.

Lee, J.H., Montagu, M.V. and Verbruggen, N. (1999) A highly conserved kinase in an essential component for stress tolerance in yeast and plant cells. Proc. Natl. Acad. Sci. USA 96: 5873-5877.

Lorz, H., Brettschneider, R., Hartke, S., Gill, R., Kranz, E., Langridge, P., Stolarz, A. and Lazzeri, P. (1990) In vitro manipulation of barley and other cereals. Stadler Genet. Symp. New York, N.Y., Plenum Press (19th). pp. 185-201.

Maheswaran, G. and Williams E.G. (1984) Direct somatic embryoid formation on immature embryos of *Trifolium repens, T. pratense* and *Medicago sativa*, and rapid clonal propagation of *T. repens*. Ann. Bol. 54: 201-211.

Maheswaran, G. and Williams, E.G. (1985) Origin and development of somatic embryoids formed directly on immature embryos of *Trifolium repens* in vitro. Ann. Bot. 56: 619-630.

Maheshwari, N., Rjyalakshmi, K., Baweja, K., Dhir, S.K., Chowdhry, C.N. and Maheshwari, S.C. (1995) in vitro culture of wheat and genetic transformation—retrospect and prospect. Crit. Rev. in Plant Sci. 14(2): 149-178.

Mannonen, L., Kauppinen, V. and Enari, T.M. (1994) Recent developments in the genetic engineering of barley. Critical Reviews in Biotechnology 14: 287-310.

Mannonen, L., Ritala, A., Salmenkallio, M., Aspegren, K., Teeri, T.H., and Kauppinen, V. (1991) Optimization of Gene Transfer in Barley by Microprojectile Bombardment. Barley Genetics VI:237-239.

McElroy, D., Zhang, W., Cao, J. and Wu, R. (1990) Isolation of an efficient actin promoter for use in rice transformation. Plant Cell 2: 163-171.

Merkle, S.A., Parrott, W.A. and Flinn, B.S. (1995) Morphogenic aspects of somatic embryogenesis. In in vitro Embryogenesis in Plants. Thorpe, T.A. Ed, Kluwer Academic Publishers. Dordracht. pp. 155-201.

Murashigue, T. and Skoog, F. (1962) A revised medium for rapid growth and bioassays with tobacco tissue cultures. Physiol. Plant. 15: 473-497.

Nehra, N.S., Chibbar, R.N., Leung, N., Caswell, K., Mallard, C., Steinhauer, L., Baga, M. and Kartha, K.K. (1994) Self-fertile transgenic wheat plants regenerated from isolated scutellar tissues following microprojectile bombardment with two distinct gene constructs. Plant J. 5: 285-297.

Paszkowski, J., Shillito, R.D., Saul, M.W., Mandak, V., Hohn, B. and Potrykus, I. (1984) Direct gene transfer to plants. EMBO J. 3: 2717-2722.

Pen, J., Sijmons, P.C., Van Ooijen, A.J.J. and Hoekema, A. (1993) Protein production in transgenic crops: analysis of plant molecular farming in transgenic plant fundamentals and applications. M. Dekker. Ed. New York. pp. 239-251.

Potrykus, I. (1990) Gene transfer to cereals: an assessment. Bio/Technol. 8(6): 535-542.

Ritala, A., Aspegren, K., Kurten, U., Salmenkallio-Marttila, M., Mannonen, L., Hannus, R., Kauppinen, V., Taeri, T.H., and Enari, T.-M. (1994) Fertile transgenic barley by particle bombardment of immature embryos. Plant Molecular Biology 24: 317-325.

Rogers, S.W. and Rogers, J.C. (1992) The importance of DNA methylation for stability of foreign DNA in barley. Plant Mol. Biol. 18:945-961.

Schaeffer, G.W., Lazar, M.D. and Baenzinger, P.S. (1984) Chapter 5—Wheat. In Handbook of Plant Cell Culture. vol. 2. Crop Species. Sharp, W.R., Evans, D.A., Ammirato, P.V. and Yamada, Y. Eds. Collier Macmillan Publishers, London, UK. pp. 108-136.

Sheveleva, E., Chmara, W., Bohnert, H.J. and Jensen, R.G. (1997) Increased salt and drought tolerance by D-ononitol production in transgenic *Nicotiana tabacum* L. Plant Physiol. 115: 1211-1219.

Spoertein, B., Mayer, A., Dahlfeld, G. and Koop, H.U. (1991) A microassay for quantitative determination of beta-glucuronidase reporter gene activitites in individually selected single higher plant cells. Plant Sci. 78(1): 73-80.

Töpler, R., Gronenborn, B., Schell, J. and Steinbiss, H.H. (1989) Uptake and Transient Expression of chimeric Genes in Seed-Derived Embryos. Plant Cell 1: 133-139.

Toyoda, H., Yamaga, T., Matsuda, Y. and Ouchi, S. (1990) Transient expression of the $\beta$-glucuronidase gene introduced into barley coleoptile cells by microinjection. Plant Cell Rep. 9: 299-302.

Wan, Y. and Lemaux, P.G. (1994) Generation of large numbers of independently transformed fertile barely plants. Plant Physiology 104: 37-48.

Weeks, J.T., Anderson, O.D. and Blechl, A.E. (1993) Rapid production of multiple independent lines of fertile transgenic wheat (*Triticum aestivum*). Plant Physiol. 102: 1077-1084.

Yao, Q.A., Simion, E., William, M., Krochko, J. and Kasha, K.J. (1997) Biolistic transformation of haploid isolated microspores of barley (*Hordeum vulgare* L.). Genome 40: 570-581.

Ahloowalia, B.S. and Maretzki, A. (1982) Plant regeneration via somatic embryogenesis in sugarcane. Plant Cell Reports 2:21-25.

Bajaj, S. and Rajam, M.V. (1995) Efficient plant regeneration from long-term callus cultures of rice by spermidine. Plant Cell Reports 14:717-720.

Chen, T., Lam, L. and Chen, S. (1985) Somatic embryogenesis and plant regeneration from cultures young inflorescences of *Oryza sativa* L. (rice). Plant Cell Tissue Organ Culture 4:51-54.

Calheiros, M.B.P. et al. 1994. Effects of exogenous polyamines on direct somatic embryogenesis in coffee. Revista Brasileira de Fisidogia Vegetal 6(2): 109-114.

Sticklen, M.B. 1991. Direct somatic embryogenesis and fertile plants from rice root cultures. J. Plant Physiol. 138(5): 577-580.

Sri Mariani Totik et al. 2000. Improvement of direct somatic embryogenesis in rice by selecting the optimal developmental stage of explant and applying desiccation treatment. Plant Production Science 3(2): 114-123.

Fernandez, Sophie et al. 1999. The embrogenic response of immature embryo cultures of durum wheat (*Triticum durum* Desf.): histology and improvement by $AgNO_3$ Plant Growth Regulation 28:147-155.

Mariani, T.S., Miyake, H. and Takeoka, Y. (1998) Changes in surface structure during direct somatic embryogenesis in rice scutellum observed by scanning electron microscopy. Plant Production Science 1:223-231. [abstract only].

* cited by examiner

PROCESS FOR INDUCING DIRECT SOMATIC EMBRYOGENESIS IN IMMATURE SCUTELLA CELLS OF POOIDEAE, AND RAPIDLY REGENERATING FERTILE PLANTS

CROSS-REFERENCE TO RELATED APPLICATION

This application is a Continuation in Part of U.S. patent application Ser. No. 09/641,243, filed Aug. 17, 2000, now abandoned, which is incorporated by reference herein to the extent that there is no inconsistency with the present disclosure.

FIELD OF THE INVENTION

The invention pertains to plant tissue culture techniques. In particular, the invention relates to processes for inducing direct somatic embryogenesis and secondary embryogenesis in monocotyledonous plant cells, and rapidly regenerating fertile plants.

BACKGROUND OF THE INVENTION

The introduction of new traits by gene transfer has become routine with respect to many dicotyledonous plant species. In contrast, monocotyledonous plant species, particularly cereals, have proven to be recalcitrant to genetic engineering because they do not belong to the natural host range of *Agrobacterium*. Therefore, unlike dicots, monocots are generally not susceptible to gene transfer by *Agrobacterium*-mediated transformation. However, the application of such methods as electroporation, PEG-mediated transformation of protoplasts, and particle bombardment, have shown promise for the stable transformation of cereals. Moreover, successful transformation of monocots using hypervirulent *Agrobacterium* strains has been recently reported.

However, the step of the introduction of foreign DNA into plant cells is only part of the equation for obtaining plants that possess new traits. It is also necessary that the transformed cells be successfully regenerated to form viable plants. Despite advances in methods for transforming monocots with foreign DNA, regeneration of fertile plants from transformed somatic cells or tissues remains a challenge, particularly in barley and wheat. One problem is that, in monocotyledonous plants, only a few somatic tissues are totipotent, i.e. capable of being regenerated to form green, fertile plants. Plants can be regenerated from totipotent cells in tissue culture by either embryogenesis or organogenesis.

i) Embryogenesis

TABLE 1

Comparison of zygotic and somatic embryogenesis (based on Dodeman et al., 1997)

| Steps | Zygotic embryogenesis | Somatic embryogenesis |
|---|---|---|
| Origin | Zygote<br>In the ovule | Somatic cell<br>Isolated or not<br>Haploid cells (e.g. microspore) |
| Initiation | Fecundation (except apomixis)<br>Every zygote<br>Constitutional polarity | Hormonal induction<br>Low cell frequency<br>Dedifferentiation<br>Polarity? |

TABLE 1-continued

Comparison of zygotic and somatic embryogenesis (based on Dodeman et al., 1997)

| Steps | Zygotic embryogenesis | Somatic embryogenesis |
|---|---|---|
| | Asymmetric division (under genetic control) | Asymmetric division? |
| Construction of an embryo | Embryo/suspensor<br>Embryo axis in place (under genetic control) | Similar conditions, but with variations:<br>Absence of the suspensor<br>Reorganization in proembryo clusters<br>Adventitious embryogenesis |
| Meristem formation | Tightly genetically controlled root meristem shoot meristem | Interaction between genetic and hormonal controls<br>Numerous abnormalities |
| Maturation | Storage protein<br>Dehydration<br>Dormancy (genetic control, ABA)<br>Plant maternal tissue-embryo interaction | Absence of maturation and endosperm<br>External induction factors (amino acids, sugars, ABA, dehydration) |

Embryogenesis is the process of embryo initiation and development, and may be classified as either zygotic or somatic, according to the type of cell from which embryogenesis arises. Features of zygotic and somatic embryogenesis are summarized in Table 1 (based on Dodeman et al., 1997).

Zygotic embryogenesis relates to embryogenesis arising from the zygote or fertilized egg which originates in the ovule, and is intrinsically embryogenic. Proliferation of the zygote leads to the formation of a zygotic embryo within which organs and tissues begin development. Within the embryo, distinctive regions, designated as the shoot and root apical meristems, promote the development of shoot and root systems respectively. Activity of the meristems contributes to the continuing expansion and formation of the plant. During the maturation stage, storage protein accumulates and dehydration enhances germination. In zygotic embryogenesis, the cells are restricted to specific fates since the developmental stages (i.e. globular, heart, torpedo, cotyledonary) are strictly genetically controlled.

In comparison, somatic embryogenesis relates to embryogenesis arising from somatic cells (i.e. vegetative or non-gametic cells), namely from isolated somatic explants or microspores. Since somatic cells are not naturally embryogenic, such cells must be induced to become embryogenic. Conversion from somatic to embryogenic cells may be achieved by external stimuli such as auxin, cytokinin, pH shifts, growth regulators, and heavy metal ions (Yeung, 1995; Dodeman et al., 1997).

Successful formation of somatic embryos is largely dependent upon the explant tissue of choice (Merkle et al., 1995). Very young zygotic embryos form somatic embryos in response to cytokinin, whereas more mature zygotic embryos no longer respond to cytokinins alone and require auxin to form somatic embryos. Meristematic cells from grasses and other monocots behave similarly. In more differentiated tissue, auxin and cytokinin induce formation of calli from which somatic embryos may be produced.

Regardless of the explant source, the obtained somatic embryo may then follow a developmental pattern similar to that of a zygotic embryo. However, unlike zygotic embryogenesis in which the developmental fate of cells is programmed, somatic embryogenesis differs in that variations and abnormalities may arise during the stages of embryo construction and meristem formation. Variations observed in vitro include the absence of the suspensor; reorganization of cells in proembryo clusters; occurrence of adventitious embryogenesis; and other abnormalities due to interaction between genetic and external hormonal controls. In zygotic embryos, activity of the meristems is crucial towards the development of the plant, whereas in somatic embryos, little is known about meristem differentiation. In comparison to zygotic embryos, maturation and storage reserves are absent in somatic embryos. Notably, somatic embryos tend to germinate precociously, with abnormalities observed such as failure or uncoordination of shoot or root formation, multiple cotyledons, or precocious or abnormal shoot formation (Wetherell, 1979). Such abnormalities are not considered problematic since in general, plantlets with normal shoots and roots eventually form (Wetherell, 1979). The fate of the cells in somatic embryos is thus not as fixed as that of cells of zygotic embryos, which follow a determined and highly regulated pathway. However, somatic embryos are beneficial for their abilities to form a complete plant despite the natural mutations that may occur in vitro, and to germinate precociously, contributing to rapid regeneration of plants.

ii) Organogenesis

As an alternative to embryogenesis, plants may also be regenerated from totipotent cells in tissue culture by organogenesis, whereby new organs such as shoots and roots, rather than whole embryos as in embryogenesis, form directly from cultured cells. The process can occur directly on the explant or indirectly via calli formation. A significant feature of organogenesis is the development of a meristem or shoot/root primodium. Only one meristem is formed in organogenesis, while two meristems (one for a shoot and the other for a root) are produced in embryogenesis. However, it is not uncommon to encounter a zygotic embryo with only one meristem (a shoot primordium) upon dissection of an immature barley embryo.

At the physiological, biochemical and structural levels, embryogenesis and organogenesis have certain common features; thus, in morphogenetic in vitro studies, it may be difficult to confirm whether somatic embryogenesis or true organogenesis has occurred (Thorpe, 1993).

Due to variations which naturally occur with somatic embryos and factors such as the explant source, media, or tissue culture technique, cells may have different developmental fates, such that some cells produce embryos (i.e. embryogenesis), while others form shoot or root primordia (i.e. organogenesis).

Although both organogenesis and embryogenesis lead to regeneration of fertile plants, embryogenesis has certain advantages. First, somatic embryos, like zygotic embryos, naturally proceed through the developmental process to form a complete plant, with little intervention. In contrast, during organogenesis, separate shoot growth and rooting steps are usually required in order to obtain complete plantlets. Second, when cultured under appropriate conditions, rather than proceeding to the next developmental stage, a somatic embryo may instead give rise to new somatic embryos. This process has been described as secondary, recurrent, or repetitive embryogenesis. Because somatic embryos can be perpetuated via repetitive embryogenesis, they are attractive candidates for the mass production of clonal plantlets.

In monocot tissue culture, the most commonly used regenerable embryogenic tissues are embryogenic suspension cells and embryogenic callus cultures. Suspension cultures are substantially homogeneous suspensions of microcalli in liquid medium. Callus cultures are grown on solid media, develop larger contiguous masses of calli, and are more heterogeneous with respect to the embryogenic quality of the calli. Both suspension cells and calli have limitations as target tissues for transformation with foreign DNA. The preparation of suspension cells involves a lengthy in vitro culture period, and the cells exhibit a significant reduction of morphogenetic competence over time. Additionally, plants regenerated from suspension cells manifest substantial undesirable somaclonal variation, such as infertility or albinism.

Because the time needed for establishment of culture and plant regeneration is shorter than with suspension cells, embryogenic callus has been considered as possibly a preferable target tissue, but problems remain. Somaclonal variation persists, and most cells lose their ability to regenerate when they reach the callus stage (Jähne et al., 1995). Despite efforts to improve callus culture, only a few monocot genotypes can be successfully regenerated from calli. In North America, the small number of genotypes which have been used successfully to regenerate fertile plants from calli include the barley genotype Golden Promise, the winter barley genotype Igri, and the wheat genotypes Fielder, Bobwhite, and Chinese Spring. Moreover, cereal calli remain embryogenic only briefly, further compounding the difficulties experienced in tissue culture.

In view of the limitations of suspension cells and callus cultures, efforts have been directed towards using primary explants such as immature embryos and inflorescences as target tissues for obtaining stably-transformed plants. However, the tissue culture techniques which have been applied to primary explants result in indirect somatic embryogenesis, wherein the intermediate cell generations between the original explant and the formation of somatic embryos are manifested as calli. Hence, indirect somatic embryogenesis from primary explants does not entirely resolve the problems associated with regeneration of plants from callus cultures.

Typically, indirect somatic embryogenesis in tissue culture involves two distinct steps, induction and regeneration. During induction, the tissue of interest is cultured on an induction medium which encourages un-differentiation of cells, and induction of fast-growing embryogenic calli. The callus stage is characterized by rapid, anarchic cell division. Tissues are cultured on the induction medium for a fixed, predetermined period, which is of sufficient duration for the production of fast growing embryogenic calli. This period typically ranges from one to four weeks (Nehra et al., 1994; Becker et al., 1994). If necessary, the tissue may be subcultured on the same medium for an additional period of time (Cho et al, 1998).

The hormone content of the media is of greatest significance. The three major classes of plant growth regulators used in tissue culture are auxins, cytokinins, and polyamines. Auxins are involved in many aspects of cell biology and tissue development. The most common are the naturally-occurring auxins indole-3-acetic acid (IAA), indole butyric acid (IBA), phenylacetic acid (PAA), and the synthetic auxins 2,4-dichlorophenoxyacetic acid (2,4-D), dicamba (2-methoxy-3,6-dichlorobenzoic acid) and picloram (4-amino-3,5,6-trichloropiconilic acid). Like auxins, cytokinins are involved in many aspects of cell biology and tissue development, especially cell division. The naturally-occurring cytokinins benzyl amino purine (BAP), benzyladenine (BA) and zeatin, and the synthetic cytokinin kinetin are the most commonly used in tissue culture. Polyamines, which include spermine, spermidine and putrescine, are less well known than other plant growth regulators. Although their precise physiological role still remains to be determined, polyamines appear to influence cell division and embryogenesis in carrot cell culture. They also bind to nucleic acids, phospholipids and proteins to further stabilize these molecules.

A typical callus induction medium for barley and wheat is Murashige and Skoog (MS) medium (Murashige and Skoog, 1962), which itself is hormone free, supplemented with 30 g/L maltose, 1.0 mg/L thiamine-HCl, 0.25 g/L myo-inositol, 1.0 g/L casein hydrolysate, 0.69 g/L proline, and 11.3 $\mu$M of dicamba (Wan and Lemaux, 1994). Other variants of basal MS medium are also known. For instance, Cho et al. (1998) describe an induction medium containing 4.5–11.3 $\mu$M 2,4-D, and 2.2 $\mu$M BAP. Nehra et al. (1994) and Bregitzer et al. (1998) teach induction media in which 9-13.6 $\mu$M 2,4-D is the only hormone component. Ritala et al. (1994) provide an induction medium in which the only plant hormone is 1.8 $\mu$M BAP. Barro et al. (1998) report that, depending on the conditions and tissues, the presence of 16.6 $\mu$M picloram can result in higher transformation efficiency than the presence of 2,4-D alone. Similarly U.S. Pat. No. 5,631,152 to Fry et al. teaches an induction medium containing 9.1 $\mu$M picloram and 2.2 $\mu$M 2,4-D.

Another basal medium commonly used for induction of callus culture is hormone free L3 medium supplemented with 30 g/L maltose and 9 $\mu$M of 2,4-D (Barcelo et al., 1993). The medium commonly used for induction of barley microspores culture is quite similar, and contains FHG basal medium supplemented with 63 g/L maltose, 730 mg/L glutamine, 100 mg/L myo-inositol, 0.4 mg/L thiamine-HCl, 4.4 $\mu$M BAP and 73.4 $\mu$M PAA (Yao et al., 1997).

In the second step, the calli are cultured on a regeneration medium such as MS, FGH, or L3. The regeneration medium is usually hormone free, though it may be supplemented with a very small amount of cytokinin and auxin, in the order of less than 4.5 $\mu$M. Termination of the auxin-mediated hormonal control allows embryogenesis to commence. As they mature, developing embryos produce shoots and regenerated plantlets. If necessary, the mass of cells with green shoots is excised and placed on a rooting medium. Rooting media typically do not contain plant hormones, although some may contain up to about 2 $\mu$M of auxin. The plantlets are then transferred to soil.

Although the two-step induction and regeneration approach to somatic embryogenesis has been applied to monocots, it has a number of significant disadvantages. First, since the induction step involves proliferation of calli, somaclonal variation remains a concern. Second, induction and regeneration are slow. Since the culture steps proceed according to a pre-determined time line, there is no opportunity to proceed more rapidly should the tissue reach the next developmental stage more quickly than anticipated. Generally, induction of calli and regeneration of green, fertile plants by indirect somatic embryogenesis takes at least three months.

In contrast to indirect somatic embryogenesis, a tissue culture process for direct somatic embryogenesis in monocotyledonous plants would advantageously avoid the callus step, thereby minimizing somaclonal variation. Moreover, such a process would also desirably eliminate the constraints of a pre-determined tissue culture schedule, thereby enabling plant regeneration to proceed as quickly as is biologically feasible. Direct somatic embryogenesis has been reported in dicots such as clover, carrot, and tobacco. For instance, Maheswaran and Williams (1984, 1985) disclose direct somatic embryogenesis of immature embryos of *Trifolium repens* (white clover), *Trifolium pratense* (red clover), and *Medicago sativa* (alfalfa) cultured on a basal nutrient medium (EC6) supplemented with 0.22 $\mu$M of the cytokinin BAP.

Despite reports of direct somatic embryogenesis in dicots, to the applicants' knowledge, direct somatic embryogenesis has not been accomplished in monocots. The patent literature discloses a number of methods for somatic embryogenesis in monocotyledonous plant tissues, but these involve a step of inducing calli, and therefore constitute indirect, rather than direct somatic embryogenesis. For instance, U.S. Pat. No. 5,631,152 to Fry et al. teaches indirect somatic embryogenesis in *Triticum aestivum*. U.S. Pat. Nos. 5,641,664 and 5,712,135 to D'Halluin et al. and U.S. Pat. No. 5,792,936 to Dudits et al., teach regeneration of corn plants from calli cells. U.S. Pat. No. 5,589,617 to Nehra et al. teaches a method for regenerating plants from wheat or barley embryos, which involves the induction of a callus stage. U.S. Pat. No. 5,610,042 to Chang et al. teaches a method for producing stably transformed fertile wheat plants involving a step of inducing formation of calli from immature wheat embryos. U.S. Pat. No. 5,874,265 to Adams et al. teaches production of stable, genetically transformed cereal plants, particularly wheat, barley, or oats, in which regeneration of plants from the transformed cells involves induction of calli. U.S. Pat. No. 4,666,844 to Cheng provides a process for regenerating cereal plants such as barley, corn, wheat, rice, and sorghum, in which tissues are first cultured under conditions sufficient to ensure calli formation. U.S. Pat. No. 5,981,842 to Wu et al. teaches the regeneration of transgenic rice (*Oryza sativa*), from calli induced from immature embryos. U.S. Pat. No. 5,409,828 to Frenkel et al. describes somatic embryogenesis in *Asparagus officinalis*, which is a monocot. But again, the first step is the induction of calli. Canadian Patent No. 1,292,959 to Stuart et al. describes somatic embryogenesis of corn and rice, again involving a callus step. International Publication No. WO 99/04618 to Rikiishi et al. discloses a method for producing transformed barley cells, which includes the step of culturing the barley cells in a calli induction medium.

Jähne et al. (1994) report some success in obtaining direct embryogenesis in barley microspores. However, microspores are germ cells, rather than somatic cells. Like other isolated germ cells, microspores are delicate relative to somatic cells, and they are very susceptible to damage by particle bombardment. Jähne et al's process is therefore of limited utility for introducing foreign genes into monocots, given that particle bombardment is the preferred transformation technique in monocots. Similarly, U.S. Pat. Nos. 5,322,789 and 5,445,961 to Genovesi et al. describe culturing corn microspores to obtain embryoids or calli.

Hence, there is a need for a tissue culture process suitable for effecting direct somatic embryogenesis in monocotyledonous plant cells or tissues and rapid regeneration of fertile plants. Ideally, in order to expedite the recovery of fertile plants, such a process would not impose predetermined time limits on the various tissue culture steps. Such a process would advantageously provide for recurrent or secondary embryogenesis from the developing embryos. In addition, such a process would also promote organogenesis in developing embryos. A direct somatic embryogenesis method for monocots would also desirably provide for the ready introduction of foreign genes into the plant.

SUMMARY OF THE INVENTION

The invention provides rapid and efficient processes for inducing direct somatic embryogenesis and secondary embryogenesis in monocotyledonous plants, particularly recalcitrant plant species such as wheat and barley, and thereafter regenerating fertile plants. In contrast to prior art tissue culture methods involving indirect somatic embryogenesis, direct somatic embryogenesis avoids a callus step, and its attendant problems, such as increased somaclonal variation. Tissue culture steps of the invention progress on the basis of the developmental stage of the cultured cells, rather than in accordance with a pre-determined time line, thereby providing green, fertile plants more rapidly than do previous tissue culture methods. In the first step, embryogenic monocotyledonous plant cells are cultured under conditions conducive to direct formation of primary embryos without an intervening callus stage. The cells are not cultured for a pre-determined period of time, but rather until a desired developmental stage is detected by observation of the cells. Preferably, the cells are cultured in the first step for a period of time sufficient for at least one primary embryo to reach the globular developmental stage. More preferably, the cells are cultured until primary embryogenesis is substantially complete, and most of the primary embryos have reached the globular developmental stage. In a second step, one or more of the globular-stage primary embryos from the first step are cultured under conditions conducive to induction of secondary embryo formation, at least until secondary embryogenesis is detected. Advantageously, the primary embryo(s) are cultured in the second step until secondary embryogenesis is well established. In a third step, the one or more secondary embryos from the second step are cultured under conditions conducive to regeneration of plantlets from the secondary embryos. Thus, in one aspect, the invention provides a process for inducing direct somatic embryogenesis and secondary embryogenesis in monocotyledonous plant cells, and rapidly regenerating fertile monocotyledonous plants, comprising the steps of:

(a) culturing embryogenic monocotyledonous plant cells under conditions conducive to direct formation of primary embryos without an intervening callus stage, at least until at least one primary embryo reaches the globular developmental stage and no longer than the coleoptilar stage of the primary embryo;

(b) culturing one or more of the primary embryos from step (a) under conditions conducive to induction of secondary embryo formation, at least until secondary embryogenesis is detected; and (c) culturing one or more of the secondary embryos from step (b) cells under conditions conducive to regeneration of plantlets from the secondary embryo.

The step of secondary embryogenesis circumvents the problem of chimeric embryos by allowing recovery of completely transformed secondary embryos from transformed sectors within a primary somatic embryo. Even if chimeric embryos are still recovered from the first cycle of secondary embryogenesis, continued cycling in the presence of a selective agent eventually results in embryos consisting entirely of transformed cells. There may be instances, however, wherein the recovery of chimeric embryos is acceptable. In such cases, the step of secondary embryogenesis can be eliminated. Thus, in another aspect, the invention provides a process for inducing direct somatic embryogenesis in monocotyledonous plant cells and rapidly regenerating fertile monocotyledonous plants, comprising the steps of:

(a) culturing embryogenic monocotyledonous plant cells under conditions conducive to direct formation of primary embryos without an intervening callus stage, at least until at least one primary embryo reaches the globular developmental stage; and (b) culturing one or more of the globular-stage primary embryos from step (a) under conditions conducive to regeneration of plantlets from the primary embryo.

Due to variations which naturally occur with somatic embryos and factors such as the species of plant and explant source, cells may have different developmental fates, such that some cells produce embryos (i.e. embryogenesis), while others form shoot or root primordia (i.e. organogenesis), as discovered by the present inventors. In particular species, organogenesis may arise following culturing of globular-stage primary embryos obtained from direct somatic embryogenesis. Organogenesis, as detected by at least the formation of adventitious shoots, occurs in species such as sorghum and corn as demonstrated in Example 4. The adventitious shoots are then cultured to regenerate plantlets. Thus, in another aspect, the invention provides a process for inducing direct somatic embryogenesis and organogenesis in monocotyledonous plant cells of particular plant species and rapidly regenerating fertile monocotyledonous plants, comprising the steps of:

(a) culturing embryogenic monocotyledonous plant cells under conditions conducive to direct formation of primary embryos without an intervening callus stage, at least until one primary embryo reaches the globular developmental stage and no longer than the coleoptilar stage of the primary embryo;

(b) culturing one or more of the primary embryos from step (a) under conditions conducive to induction of organogenesis, at least until adventitious shoots are detected; and (c) culturing one or more of the adventitious shoots from step (b) under conditions conducive to regeneration of plantlets.

The foregoing aspects of the invention are directed principally to inducing direct somatic embryogenesis in primary explants such as, without limitation, immature embryos, meristems, and inflorescenses. However, aspects of the invention may also be used for rapidly inducing embryogenesis in embryogenic monocotyledonous callus cells, suspension cells, or microspore-derived embryos. In such instances, the step of direct somatic embryogenesis is omitted, and the callus cells, suspension cells, or microspore-derived embryos are cultured first in the presence of such amounts of plant hormones that would otherwise be used to induce secondary embryogenesis. Hence, in another aspect, the invention provides a process for inducing somatic embryogenesis in monocotyledonous callus cells, suspension cells, or microspore-derived embryos, and rapidly regenerating fertile monocotyledonous plants, comprising the steps of:

(a) culturing embryogenic monocotyledonous callus cells, suspension cells or microspore-derived embryos in or on a culture medium comprising auxin, cytokinin, and polyamine in amounts effective to cause induction of embryo formation, the cytokinin being present in greater proportion than the auxin, at least until at least one embryo reaches the globular developmental stage; and (b) cultivating one or more of the globular-stage embryos from step (a) under conditions conducive to regeneration of plantlets.

The invention also extend to the use of preferred culture media with specific plant hormones for the various stages of the embryogenesis processes set out above.

Also provided are fertile monocotyledonous plants produced according to the foregoing processes, and methods of transforming such plants to introduce foreign DNA so that the foreign DNA becomes stably integrated into the genome of the embryogenic cells.

As used herein and in the claims, the terms and phrases set out below have the meanings which follow.

"Embryogenesis" means the process of embryo initiation and development.

"Embryogenic," in the context of cells or tissues, means that the cells or tissues can be induced to form viable plant embryos, under appropriate culture conditions.

"Explant" means tissue taken from its original site and transferred to an artificial medium for growth or maintenance.

"Induction" means initiation of a structure, organ or process in vitro.

"Regeneration" means a morphogenetic response to a stimulus that results in the production or organs, embryos, or whole plants.

"Germination" means the growth of leaves and roots from the germ or embryo.

"Plantlet" means a small regenerated plant with green shoots and roots.

"Callus" or "calli" means a mass of unorganized tissues made up of undifferentiated cells that normally divide very rapidly.

"Suspension cells" or "suspension culture" refers to a substantially homogeneous suspension of microcalli in liquid medium.

"Microspore-derived embryo" refers to an embryo which arises from an induced microspore in anther culture or isolated microspore culture.

"Auxin" is meant to include naturally-occurring auxins such as, without limitation, indole-3-acetic acid (IAA), IAA conjugated with an amino acid, indole 3-butyric acid (IBA), indole 3-butyric acid-potassium salt (KIBA), phenylacetic acid (PAA), and synthetic auxins such as, without limitation, 2,4-dichlorophenoxyacetic acid (2,4-D), dicamba (2-methoxy-3,6-dichlorobenzoic acid), picloram (4-amino-3,5,6-trichloropiconilic acid), 4-chlorophenoxyacetic acid (CPA), α-napthaleneacetic acid (NAA), and β-napthoxyacetic acid (NOA), or combinations thereof.

"Cytokinin" is meant to include naturally occurring cytokinins such as, without limitation, benzyl amino purine (BAP), 6-benzylaminopurine (BA), 6-benylaminopurine riboside (BAR), 6-(γ,γ-dimethylallylamino) purine (2iP), 6-(γ,γ-dimethylallylamino) purine riboside (2iP-R), N-(2-chloro-4-pyridyl)-N'-phenylurea (4-CPPU) zeatin, zeatin riboside (ZR), dihydrozeatin, and thidiazuron, and synthetic cytokinins such as, without limitation kinetin and kinetin riboside (KR), or combinations thereof.

"Polyamine" is meant to include, without limitation, the plant growth regulators spermine, spermidine, putrescine, and cadaverine.

"Somatic embryogenesis" means the formation of embryos from vegetative (or non-gametic tissues) with 2n chromosomes, rather than by sexual reproduction.

"Direct somatic embryogenesis" means a form of embryogenesis wherein embryos develop from vegetative cells without an intervening callus step or stage.

"Indirect somatic embryogenesis" means a form of embryogenesis wherein embryos develop from callus tissues induced in vitro.

"About," when used to describe a concentration of auxin, cytokinin, or polyamine, means ±10%.

"Primary embryogenesis" is meant to refer to a first stage or cycle of somatic embryogenesis, in which the embryos which are formed are referred to as "primary embryos."

"Secondary embryogenesis" is meant to refer to a second stage or cycle of somatic embryogenesis to give rise to new somatic embryos, which are termed "secondary embryos."

"Organogenesis" is meant to refer to induction of new organs, such as new adventitious shoots or roots.

"Adventitious" means developing from unusual points of origin, such as shoots or root tissues from calli, or embryos from sources other than zygotes.

A medium that is "essentially free" of auxin or cytokinin means a medium that, if auxin and/or cytokinin is present at all, it is present at a sufficiently low level that it does not effect hormonal control over the cultured cells.

"Foreign DNA" and "foreign gene," when used in the context of transforming target plant cells, is meant to encompass not only DNA which originates from sources other than the target plant, but also encompasses DNA which originates from the target plant but that has been introduced or manipulated "by the hand of man" such that it exists in an arrangement or juxtaposition other than it exists in nature (e.g. such as DNA inserted into a vector).

"Molecular farming" means the use of transgenic plants to produce large quantities of a desired gene product.

BRIEF DESCRIPTION OF THE DRAWINGS

FIGS. 1 and 2 are scanning electron microscopy images of barley scutella at various stages of direct somatic embryogenesis and secondary embryogenesis, in which:

FIG. 1 shows an immature scutellum at the time of culture initiation, prior to the commencement of embryogenesis.

FIG. 2 shows the immature scutellum after five days of culture, at which time direct somatic embryogenesis has commenced. Globular primary embryos 12 and a small amount of calli 10 are observed on different tissue parts of the scutellum.

Figure 1:
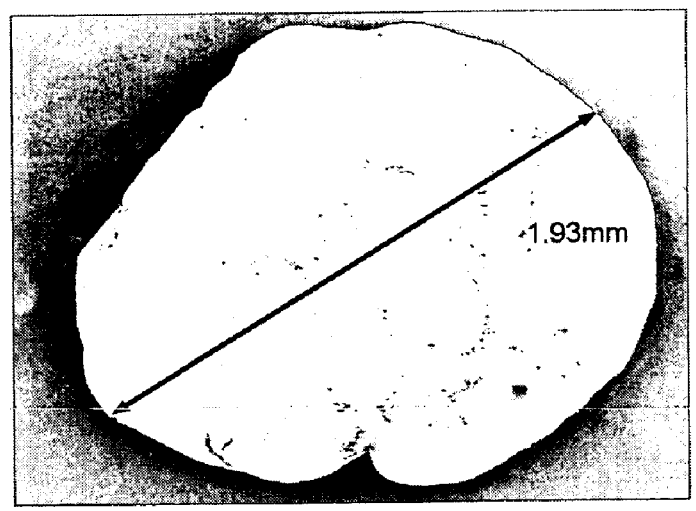

DETAILED DESCRIPTION OF THE INVENTION i) Isolation of Primar Explants

The processes of the invention are useful for inducing direct somatic embryogenesis in a wide range of monocotyledonous plants. Monocotyledonous plants (i.e. monocots) are distinguished from dicotyledonous plants (i.e. dicots) principally on the basis that the seed of a monocot contains a single cotyledon, whereas that of a dicot contains two cotyledons. The invention is of particular benefit when applied to monocotyledonous plants within the Poaceae family. These plants have proven to be recalcitrant to other tissue culture techniques. Preferred Poaceae include common wheat (*Triticum aestivum*), durum wheat (*Triticum durum*), *Triticum monococum*, *Triticum urartu*, barley (*Hordeum vulgare*), rye (*Secale cereale*), oat (*Avena sativa*), triticale, corn (*Zea mays*), rice (*Oryza sativa*), sorghum (*Sorghum vulgare*), millet (*Pennesitum glaucum* and *Pennesitum purpureum*), and sugarcane (*Saccharum officinale*), many of which have responded poorly in the past to tissue culture. The invention can also be applied to other monocots, including, without limitation: members of the Liliaceae family, particularly members of the genus *Allium*, such as garlic, leek, onion, and chive; and other members of the Poaceae family, particularly members of the genera *Dactylis* (e.g. orchard grass), *Bromus* (e.g. brome), and *Lolium* (e.g. perennial rye grass), or festuca. The processes of the invention are genotype independent, and can be applied, in the case of, for instance, barley or wheat, to all barley and wheat varieties, including malting barley (e.g., cv Harrington), feed barley (e.g., cv AC Lacombe) and forage barley (e.g., T89043003NX), wheat (e.g., cvs AC Nanda and AC Fielder) and durum wheat amphiploids.

Any plant cells or tissues which remain embryogenic, or which can be induced to return to an embryogenic state, can be used. Such cells or tissues can be induced to form viable plant embryos under appropriate culture conditions. Preferred primary explants include, without limitation, immature embryos, inflorescences, immature inflorescences, and meristems. In cereals, a scutellum isolated from an immature embryo may have a preferred length of 1–2.5 mm, but a length of 1.5–2 mm (about 14 days post-anthesis) is most preferred. A scutellum is a modified leaf, which is the equivalent of the cotyledon in dicots. The scutellum nourishes the germ during embryogenesis and during germination. Monocotyledonous embryos progress through globular, coleoptilar, and scutellar stages (Carman, 1990; Merkle et al., 1995).

Although it is desirable to separate the germ from the scutellum, care should be taken to avoid damaging the scutellum. In order to remove the germ from the embryo, a hook-shaped blade, in which the hook is sized to match the size of the germ, that is which has a radius of curvature to match the outer surface of the germ to be extracted, may advantageously be used. The germ should be removed cleanly, without damaging the scutellum. This prevents the embryo axis (the germ) from interacting with the development of the scutellum cells, thereby avoiding the need for later dissection to remove germinating shoots and roots from the plated embryo.

In other aspects, the invention is useful for inducing embryogenesis in callus cells, suspension cells, and microspore-derived embryos. Callus or calli is a mass of unorganized tissues made up of undifferentiated cells that normally divide very rapidly. Callus is usually induced by the presence of auxin. It also typically forms as a response of tissues to stress, and occasionally develops on a wound in vivo. Suspension cells or suspension cultures comprise substantially homogeneous suspensions of microcalli in liquid medium, whereas a microspore-derived embryo arises from an induced microspore in anther culture or isolated microspore culture. Procedures for obtaining callus cells, suspension cells, or microspore-derived embryos of monocotyledonous plants are known in the art (Lorz et al., 1990; Maheshwari et al., 1995; Bhaskaran et al., 1990).

ii) Tissue Culture Media

Plant tissue culture media typically include substances that can be categorized into seven groups, as follows: salts, sugars, amino acids, hormones (i.e. plant growth regulators), organic acids, vitamins, and gel. Without being bound by same, it is believed that, in the present invention, it is the plant hormone composition of the media that is of greatest significance. In each of the media described herein and in subsequent steps, a wide variety of each of salts, sugars, amino acids, organic acids, and vitamins have been provided in the media to ensure that the media is not deficient in any of these aspects. By and large, for the purposes of the invention, any particular salt, sugar, amino acid, organic acid, or vitamin could be replaced by an alternative, functionally equivalent salt, sugar, amino acid, organic acid, or vitamin, as are known in the art, without a negative effect. Useful basal media include MS (Murashige and Skoog, 1962), and B5 (Gamborg et al., 1968) which are good tissue culture media for most monocot species. George et al. (1987) provide a useful compendium of plant culture media and suitable applications. As salts, sugars, amino acids, organic acids, and vitamins have been included in the media exemplified herein with a view to creating redundancy and excess, one or more of the specified salts, sugars, amino acids, organic acids, or vitamins likely may be reduced in quantity or eliminated, without adverse effect. Tissue culture media may be liquid, solid, or semi-solid. Those skilled in the art can manipulate these aspects of the media formulations and adapt them as needed, within the scope of the invention. All components of plant tissue culture media described herein can be purchased from Sigma-Aldrich, Inc. (St. Louis, Mo., USA).

Tissue culture media used in the invention contain plant growth regulators categorized as auxins, cytokinins, and polyamines. Auxins comprise a family of compounds grouped by function, and which do not share a common chemical structure. Compounds are generally considered to be auxins if they can be characterized by their ability to induce cell elongation in stems and otherwise resemble indoleacetic acid (the first auxin isolated) in physiological activity (Arteca, 1996). Auxins thus may include naturally-occurring auxins such as, without limitation, indole-3-acetic acid (IAA), IAA conjugated with an amino acid, indole 3-butyric acid (IBA), indole 3-butyric acid-potassium salt (KIBA), phenylacetic acid (PAA), and synthetic auxins such as, without limitation, 2,4-dichlorophenoxyacetic acid (2,4-D), dicamba (2-methoxy-3,6-dichlorobenzoic acid), picloram (4-amino-3,5,6-trichloropiconilic acid), 4-chlorophenoxyacetic acid (CPA), α-napthaleneacetic acid (NAA), and β-napthoxyacetic acid (NOA), or combinations thereof. Particularly preferred auxins are 2,4-D and PAA.

Like auxins, cytokinins encompass disparate chemical structures, though many have a structure resembling adenine. Cytokinins promote cell division, and have other functions similar to those of kinetin. Kinetin was the first cytokinin discovered, and was so named because of its ability to promote cytokinesis (i.e. cell division). Though it is a natural compound, kinetin is not produced in plants, and is therefore usually considered a "synthetic" cytokinin (i.e. the hormone is synthesized by an organism other than a plant). The most common form of naturally occurring cytokinin in plants is zeatin, which was isolated from corn (*Zea mays*). Cytokinins have been found in almost all higher plants as well as mosses, fungi, bacteria, and also in tRNA of many prokaryotes and eukaryotes. In excess of 200 natural and synthetic cytokinins are known. Cytokinin concentrations are highest in meristematic regions and areas of continuous growth potential such as roots, young leaves, developing fruits, and seeds (Arteca, 1996). Cytokinins may include naturally occurring cytokinins such as, without limitation, benzyl amino purine (BAP), 6-benzylaminopurine (BA), 6-benylaminopurine riboside (BAR), 6-(γ,γ-dimethylallylamino) purine (2iP), 6-(γ,γ-dimethylallylamino) purine riboside (2iP-R), N-(2-chloro-4-pyridyl)-N'-phenylurea (4-CPPU) zeatin, zeatin riboside (ZR), dihydrozeatin, and thidiazuron, and synthetic cytokinins such as, without limitation kinetin and kinetin riboside (KR), or combinations thereof. A particularly preferred cytokinin is BAP.

There is some controversy as to whether polyamines should be classified as plant hormones. They are widespread in all cells, and they exert regulatory control over growth and development, even at very low levels. Polyamines have a wide range of effects on plants, and they appear to be essential in growth and cell division. Unlike auxins and cytokinins, the polyamines known to function as plant hormones are all related, naturally-occurring compounds found in the same biosynthetic pathway. Such polyamines include, without limitation, the plant growth regulators spermine, spermidine, putrescine, and cadaverine, with spermine and spermidine being particularly preferred.

The plant growth regulators may be present in the media in the form of a single compound within a hormone class (e.g. the auxin component consists only of 2,4-D), or as a combination of compounds (e.g. the auxin component includes both 2,4-D and picloram). Although the compounds within a hormone class are believed to be largely interchangeable, it is believed that the polyamines are an exception, and that spermine and spermidine are functionally distinct from putrescine and cadaverine as plant hormones. Although spermine and spermidine may be used interchangeably in the invention, it is believed that neither putrescine or cadaverine can entirely replace spermine or spermidine in the media. All of the plant growth regulators described herein may be obtained from Sigma-Aldrich, Inc. (St. Louis, Mo., USA).

iii) Direct Somatic Embryogenesis

In one aspect of the invention, the embryogenic monocotyledonous plant cells are first cultured under conditions conducive to direct formation of primary somatic embryos without an intervening callus stage. Somatic embryogenesis is the formation of embryos from vegetative tissues with 2n chromosomes, rather than by sexual reproduction. Somatic embryos originate from small clusters of undifferentiated cells or single cells, and are morphologically analogous to zygotic (fertilized) plant embryos formed through sexual reproduction. Somatic embryos develop normally, and produce plants that are indistinguishable from those obtained from zygotic embryos. Direct somatic embryogenesis describes a form of embryogenesis wherein embryos develop from vegetative cells without an intervening callus step or stage. In contrast, indirect somatic embryogenesis occurs when embryos develop from callus tissues induced in vitro. Elimination of a callus stage through direct somatic embryogenesis advantageously avoids undesirable somaclonal variation. This can be accomplished by cultivating the cells in or on a culture medium which contains plant hormones in concentrations and relative proportions as described herein.

In order to induce direct somatic embryogenesis, the cells are cultured on or in media containing auxin, cytokinin, and polyamine, wherein auxin is present in greater proportion than cytokinin. Preferably, the ratio of auxin to cytokinin in the culture medium is from about 5 $\mu$M auxin per 1 $\mu$M cytokinin to about 20 $\mu$M auxin per 1 $\mu$M cytokinin, and is more preferably about 14 $\mu$M auxin per 1 $\mu$M cytokinin.

In absolute terms, the medium preferably contains: from about 15 $\mu$M to about 45 $\mu$M auxin; from about 15 $\mu$M polyamine to about 45 $\mu$M polyamine; and, from about 1 $\mu$M cytokinin to about 5 $\mu$M cytokinin. More preferably, the culture medium contains: about 30 $\mu$M auxin; about 30 $\mu$M polyamine; and, about 2 $\mu$M cytokinin.

In an exemplified case, the medium is "DSEM" medium, the composition of which is specified in Table 2 herein.

Those of ordinary skill in the art will appreciate that the composition of the DSEM medium, particularly with respect to the salts, sugars, amino acids, organic acids, vitamins, and gel, can be modified or adapted without departing from the scope and spirit of the invention.

Figure 2:

The cells are not cultured for a pre-determined period of time, but rather at least until, as determined by observation, at least one primary embryo reaches the globular developmental stage. FIG. 1 illustrates an immature barley scutellum at the time of culture initiation, prior to the commencement of embryogenesis. The immature scutellum appears to lack distinct structures. However, FIG. 2 shows the immature scutellum after five days of culture, at which time direct somatic embryogenesis has commenced since numerous primary embryos at the globular developmental stage are observed. These globular embryos 12 may be recognized by their spherical shape on the surface of the scutellum. A small amount of calli 10, which appears soft and friable, is present on a different part of the scutellum. To assess developmental stage, the tissues may thus be examined for such characteristic features under a stereo-microscope.

Proceeding on the basis of developmental stage, rather than in accordance with a rigid time table, enables the processes of the invention to provide fertile, green plants faster than do prior art techniques. Typically, many primary embryos will reach the globular developmental stage simultaneously, but the developmental rate of all primary embryos will not be identical. It is sufficient that the cells remain on the first culture medium until at least one primary embryo reaches the globular developmental stage. However, if the number of secondary embryos to be obtained in a subsequent step of secondary embryogenesis is to be maximized, and the overall time to obtain fertile plants is of lesser concern, the cells may be cultured longer, up until the point that primary embryos reach the coleoptilar stage. FIG. 2 depicts well the point at which transfer of the globular-stage primary embryos to a culture for secondary embryogenesis is desirable.

iv) Secondary Embryogenesis

A significant advantage of somatic embryogenesis is that it provides an opportunity for manipulating primary embryos such that, rather than proceeding to the next stage in their ontogeny, they instead give rise to new somatic embryos (i.e. recurrent or secondary embryogenesis). The proliferation of embryos can be exploited for mass propagation and the production of transgenic plants. Secondary embryogenesis is, however, an optional step in the invention. There may be occasions where it is instead desired to proceed directly to the step of regeneration of plantlets.

Figure 3:
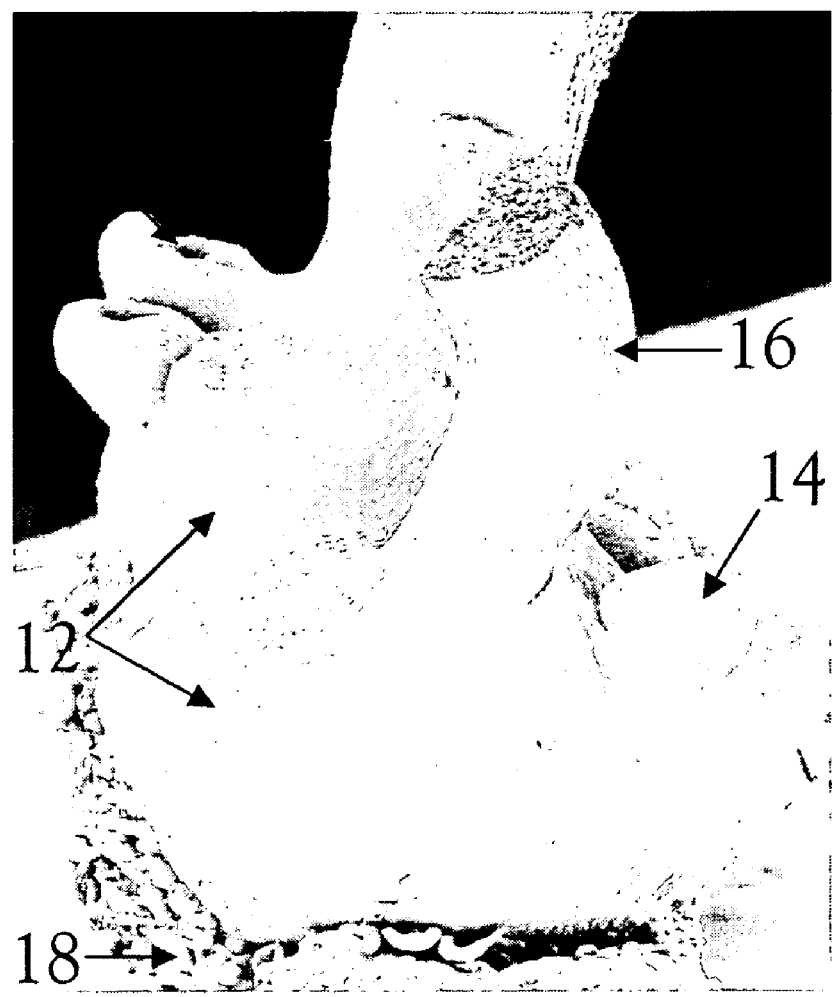
FIG. 3 is a scanning electron microscopy image depicting stages of direct somatic embryogenesis and secondary embryogenesis in wheat, showing germinating primary embryos 12 with secondary embryos 14 arising at the equatorial plane, and primary leaves 16 and a small amount of tissue remaining from the scutellum 18.

If secondary embryogenesis is desired, in accordance with the invention, the embryogenic cells, in which direct somatic embryogenesis has been induced, are cultured under conditions conducive to induction of secondary embryo formation, for a period of time that persists at least until secondary embryogenesis is detected. The length of the secondary embryogenesis culture step is determined by observation of the cultured tissues, rather than in accordance with a pre-determined time line. Although it may be desired to continue culturing secondary embryos for repetitive cycles of embryogenesis, cells may be transferred to the next step once secondary embryogenesis can first be detected with the use of a stereo-microscope. In this respect, FIG. 3 illustrates secondary embryogenesis in wheat. Secondary embryos 14 arise at the equatorial plane of a germinating primary embryo 12. They initially appear as bulges growing at the surface of the germinating primary embryo, and soon switch to the coleoptilar stage. The coleoptilar stage is signified by the appearance of primordium of coleoptiles which may appear partly circular, perfectly circular, or more complex in shape and may cover the meristem and first leaf of the embryo. Primary leaves 16 and a small amount of tissue remaining from the scutellum 18 are indicated. Typically, the cells will be cultured under conditions conducive to secondary embryogenesis at least until a first generation of secondary embryos is well-developed. FIG. 3 is a good illustration of the point at which transfer of the secondary embryos to a culture medium conducive to regeneration of plantlets is desirable.

"Primary embryogenesis" refers a first stage or cycle of somatic embryogenesis, in which the embryos which are formed are referred to as "primary embryos." "Secondary embryogenesis" refers to a second stage or cycle of somatic embryogenesis to give rise to new somatic embryos, termed "secondary embryos."

In order to induce secondary embryogenesis, the cells are cultured in or on a solid, semi-solid or liquid medium containing auxin, cytokinin, and polyamine, wherein cytokinin is present in greater proportion than auxin.

Preferably, the ratio of auxin to cytokinin in the culture medium used to induce secondary embryogenesis is from about 0.05 $\mu$M auxin per 1 $\mu$M cytokinin to about 0.2 $\mu$M auxin per 1 $\mu$M cytokinin, and is more preferably about 0.1 $\mu$M auxin per 1.0 $\mu$M cytokinin.

In absolute terms, the secondary enibryogenesis medium preferably contains: from about 5 $\mu$M auxin to about 15 $\mu$M auxin; from about 15 $\mu$M polyamine to about 45 $\mu$M polyamine; and, from about 50 $\mu$M cytokinin to about 200 $\mu$M cytokinin. More preferably, the culture medium contains: about 11 $\mu$M auxin; about 30 $\mu$M polyamine; and, about 110 $\mu$M cytokinin.

In an exemplified case, the medium is "SEM" medium, the composition of which is specified in Table 2 herein. Those of ordinary skill in the art will appreciate that the composition of the SEM medium, particularly with respect to the salts, sugars, amino acids, organic acids, vitamins, and gel, can be modified or adapted without departing from the scope and spirit of the invention.

In another aspect of the invention, there are circumstances wherein the step of secondary embryogenesis may not be needed or desired, and it is possible to proceed directly from direct somatic embryogenesis to the step of germination or regeneration. For example, the processes of the invention are useful in connection with screening procedures, wherein plants are to be tested for tolerance to certain substances, such as salt, or compounds involved in disease conditions (e.g. trichothecenes for fusarium heat blight (FHB) resistance). If the plant cells are transformed with foreign genes, the step of secondary embryogenesis would generally be of benefit for reducing the number of chimeric plants regenerated and obtaining more green and fertile plants. If, however, chimeric plants are not unacceptable, the cells may be transferred directly from the direct somatic embryogenesis culture conditions to germination or regeneration.

v) Organogenesis

Due to variations which naturally occur with somatic embryos and factors such as the species of plant and explant source, cells may have different developmental fates, such that some cells produce embryos (i.e. embryogenesis), while others form shoot or root primordia (i.e. organogenesis). While primary embryos, for example of barley, wheat, oat, rye, and durum wheat as demonstrated in Examples 1, 2 and 3, form secondary embryos under appropriate culture conditions, other species, such as sorghum and corn as reported in Example 4, react differently to the same culture conditions. Organogenesis refers to induction of new organs, such as new adventitious shoots or roots. As reported herein, organogenesis may arise following culturing of globular-stage primary embryos obtained from direct somatic embryogenesis. Organogenesis, as detected by at least the formation of adventitious shoots, may occur in species such as sorghum and corn as demonstrated in Example 4. The adventitious shoots are then cultured to regenerate plantlets. Thus, it appears possible to regenerate plantlets of particular plant species, such as sorghum and corn genotypes as reported herein, through the processes of direct somatic embryogenesis and organogenesis.

The embryogenic monocotyledonous plant cells are first cultured under conditions conducive to direct formation of primary somatic embryos without an intervening callus stage, as described previously. Briefly, the cells are cultured on or in media containing auxin, cytokinin, and polyamine, wherein auxin is present in greater proportion than cytokinin.

Preferably, the ratio of auxin to cytokinin in the culture medium is from about 5 $\mu$M auxin per 1 $\mu$M cytokinin to about 20 $\mu$M auxin per 1 $\mu$M cytokinin, and is more preferably about 14 $\mu$M auxin per 1 $\mu$M cytokinin.

In absolute terms, the medium preferably contains: from about 15 $\mu$M to about 45 $\mu$M auxin; from about 15 $\mu$M polyamine to about 45 $\mu$M polyamine; and, from about 1 $\mu$M cytokinin to about 5 $\mu$M cytokinin. More preferably, the culture medium contains: about 30 $\mu$M auxin; about 30 $\mu$M polyamine; and, about 2 $\mu$M cytokinin.

In an exemplified case, the medium is "DSEM" medium, the composition of which is specified in Table 2 herein. Those of ordinary skill in the art will appreciate that the composition of the DSEM medium, particularly with respect to the salts, sugars, amino acids, organic acids, vitamins, and gel, can be modified or adapted without departing from the scope and spirit of the invention.

In order to induce organogenesis, the globular-stage primary embryos are then cultured on or in media containing auxin, cytokinin, and polyamine, wherein cytokinin is present in greater proportion than auxin.

Preferably, the ratio of auxin to cytokinin in the culture medium is from about 0.05 $\mu$M auxin per 1 $\mu$M cytokinin to about 0.2 $\mu$M auxin per 1 $\mu$M cytokinin, and is more preferably about 0.1 $\mu$M auxin per 1.0 $\mu$M cytokinin.

In absolute terms, the medium preferably contains: from about 5 $\mu$M to about 15 $\mu$M auxin; from about 15 $\mu$M polyamine to about 45 $\mu$M polyamine; and, from about 50 $\mu$M cytokinin to about 200 $\mu$M cytokinin. More preferably, the culture medium contains: about 11 $\mu$M auxin; about 30 $\mu$M polyamine; and, about 110 $\mu$M cytokinin.

In an exemplified case, the medium is "SEM" medium, the composition of which is specified in Table 2 herein. Those skilled in the art will appreciate that the composition of the SEM medium, particularly with respect to the salts, sugars, amino acids, organic acids, vitamins, and gel, can be modified or adapted without departing from the scope and spirit of the invention.

The globular-stage primary embryos are cultured until induction of organogenesis or the formation of new organs, as detected by the presence of adventitious shoots. The new shoots obtained are cultured in or on regeneration medium to produce plantlets. Preferably, the medium is $MS_{reg}$, the composition of which is set forth in Table 2 herein. The plantlets and shoots are cultured under conditions conducive to root formation, after which the plantlets are transplanted to soil and grown to maturity.

vi) Induction of Embryogenesis in Embryogenic Monocotyledonous Callus Cells, Suspension Cells, or Microspore-derived Embryos The foregoing aspects of the invention are directed principally to inducing direct somatic embryogenesis in primary explants, such as immature embryos, meristems, and inflorescences. However, aspects of the invention may also be used for rapidly inducing embryogenesis in embryogenic monocotyledonous callus cells, suspension cells, or microspore-derived embryos.

In yet another aspect of the invention, when working with callus cultures or suspension cells or microspore-derived embryos, the step of direct somatic embryogenesis is eliminated. The monocotyledonous plant cells of interest are cultured under SEM medium followed by a germination or regeneration step. This approach is useful as an alternative to the standard two-step induction and regeneration process. Embryogenesis is induced by culturing the cells in or on a medium containing auxin, cytokinin, and polyamine, wherein cytokinin is present in greater proportion than auxin, as described above in this section. Preferred media compositions are also as described hereinbefore. If the cells of interest are callus or suspension cells, the resulting embryogenesis cannot properly be characterized as primary or secondary embryogenesis, but merely as embryogenesis. The cells may be transferred to the regeneration step once embryogenesis is detected. Preferably, however, the cells are not transferred to the next step until embryogenesis is substantially complete. If microspore-derived embryos are used as the starting material, the result is secondary embryogenesis, much as if the tissues had been transferred from the step of direct somatic embryogenesis.

vii) Germination

In some instances, it may be advantageous, after the step of secondary embryogenesis (or, if secondary embryogenesis is excluded -then after the step of direct somatic embryogenesis) to cultivate the cells under conditions conducive to germination of the primary or secondary embryos. For this purpose, a solid, semi-solid or liquid culture medium containing polyamine in amount effective to cause germination of the embryos, and which is essentially free of either auxin or cytokinin, is preferred. Preferably, the germination medium contains from about 15 $\mu$M polyamine to about 45 $\mu$M polyamine, more preferably about 30 $\mu$M polyamine. In a preferred embodiment, the germination medium is "GEM" medium, the composition of which is described in Table 2 herein. It will be understood that the composition of the GEM media, apart from the plant hormone component, is not essential, and that it may be adapted or optimized to meet the requirements of particular circumstances without departing from the invention.

Cells are cultured on the germination medium until germination of at least one embryo commences. Germination is the growth of leaves and roots from the germ. Preferably, the developing embryos are cultured until the germination has commenced in a majority of embryos, though a lesser degree of germination may be sufficient. Once a satisfactory degree of germination has been established, the cells can be transferred to the regeneration step.

viii) Regeneration

In order to produce plantlets, the developing embryos are preferably cultured in or on a regeneration medium. A variety of suitable regeneration media are known in the art as described by George et al. (1987). The choice of regeneration medium is not critical. A particularly suitable regeneration medium is $MS_{reg}$ (Murashige and Skoog, 1962), the composition of which is set forth in Table 2 herein. The low auxin concentration of $MS_{reg}$ favours the formation of green shoots from primary and secondary embryos.

Root initiation and development in wheat tissues often occurs during the regeneration step. In that case, once root formation is established, the developing plantlets can be directly transferred to pots containing potting mix. The choice of potting mix is not critical, and many are known in the art. For instance, a suitable potting mix is Cornell mix.

There may be instances wherein root development does not initiate during the regeneration step. This is often the case with barley tissues, for example. If roots do not develop on regeneration media, a mass of cells forming green shoots is placed on a last medium for root initiation. Suitable rooting media include MS, or a half dose of MS (Ahloowalia, 1982), the rooting medium of Green (1982), or rooting medium R of Schaeffer et al. (1984). Once roots have been established, plantlets are transferred to potting mix.

ix) Transformation

The processes of the invention are particularly useful in connection with the introduction of foreign genes or DNA into monocot plant cells. Foreign genes which may be introduced into plants in accordance with the invention include, without limitation, genes related to quality traits, disease or pathogen resistance genes, stress resistance genes, herbicide resistance genes, and genes which are introduced into plants for large-scale recovery of the encoded product by molecular farming.

Genes relating to quality traits include, for instance, $\beta$-glucanase genes (e.g. egl1), which have been introduced into barley plants in order to improve malting (Mannonen, 1993). Genes encoding other enzymes, such as xylanases, or phytases, may be introduced into plants to increase their digestibility or phosphate absorption when used as animal feeds. An interesting example of a quality trait introduced into a cereal crop plant is the introduction into rice of a gene encoding the last enzyme in the pathway for vitamin A biosynthesis (Burkhardt et al., 1997). The resulting transgenic rice may be beneficial in the Third World for preventing blindness in children, a condition which often results from vitamin A deficiency.

A number of disease resistance genes have been introduced into plants, and may be used in connection with the invention. Examples include the barley yellow dwarf virus resistance gene (BYDV) (Wan and Lemaux, 1994), the thaumatin fungal resistance gene (Rogers and Rogers, 1992), and the stripe rust resistance gene (Yr10), which is exemplified in the Examples herein. Other disease resistance genes which may be introduced into plants in accordance with the invention are known in the art, a number of which are enumerated by Mannonen et al. (1994). Alternatively, the foreign gene may confer resistance to insects or other pests. Such genes include, without limitation, those that encode enzyme inhibitors, insect-specific hormones or pheromones, insect-specific peptides or neuropeptides which disrupt the physiology of the targeted pest, or an insect-specific poison or venom produced in nature.

Herbicide resistance genes are known in the art, and may be introduced into plants in accordance with the processes of the invention. Examples include: CP4, a bacterial 5-enolpyruvylshikimate-3-phosphate synthase (EPSPS) gene which expresses an enzyme highly resistant to glyphosate, the active ingredient in the herbicide ROUND-UP™;

the glyphosate oxidoreductase (GOX) gene, which is a bacterial gene which degrades glyphosate into aminomethyl phosphoric acid (U.S. Pat. No. 5,631,152 to Fry et al.); and the bar gene, which provides resistance to glufosinate ammonium, the active ingredient in LIBERTY™ herbicide.

Genes which confer stress resistance properties may be introduced into monocotyledonous plants in accordance with the invention. Desirable stress-resistance properties include, without limitation, salt tolerance (Lee et al., 1999), drought tolerance (Sheveleva et al., 1997), cold tolerance (Hayashi et al., 1997), and heavy metal tolerance, such as aluminum tolerance (De La Fuente et al., 1997)

Involving the use of transgenic plants to produce large quantities of a desired gene product, molecular farming has many advantages over traditional microbial fermentation systems, including elimination of the requirements for extrinsic energy sources, sophisticated fermentation apparatus, and closely controlled culture conditions. Plants transformed in accordance with the invention may be used for such disparate purposes as making therapeutic proteins, enzymes, antibodies, vaccines, or making biodegradable plastics (Fischer et al., 1999; Elliott et al., 1996; Hemming, 1995; Pen et al., 1993).

Vectors for introducing foreign DNA into plant cells are well known in the art (Gruber et al. (1993). Suitable recombinant vectors include an expression cassette designed for initiating transcription of the foreign DNA in plants. Additional sequences can be included to allow the vector to be cloned in a bacterial or phage host. The vector will preferably contain a prokaryote origin of replication having a broad host range. A selectable marker may also be included to allow selection of bacterial cells bearing the desired construct. Suitable prokaryotic selectable markers include those that confer resistance to antibiotics such as ampicillin. Other DNA sequences encoding additional functions may also be present in the vector. For instance, in the case of *Agrobacterium*-mediated transformation, T-DNA sequences will also be included for subsequent transfer to plant chromosomes.

For expression in plants, the recombinant expression cassette preferably contains, in addition to the desired gene sequence to be expressed, a promoter region effective in plants, a transcription initiation site (if the sequence to be transcribed lacks one), and a transcription termination sequence. Unique restriction enzyme sites at the 5' and 3' ends of the cassette are typically included to allow for easy insertion into a pre-existing vector. Sequences controlling eukaryotic gene expression are well known in the art.

The particular promoter used in the expression cassette is not critical to the invention. Any of a number of promoters which direct transcription in monocotyledonous plant cells is suitable. The promoter can be either constitutive, inducible, tissue specific, or temporal specific. A number of promoters which are active in plant cells have been described in the literature, including the nopaline synthase (NOS) and octopine synthase (OCS) promoters (which are carried on tumour-inducing plasmids of *Agrobacterium tumefaciens*), the caulimovirus promoters such as the cauliflower mosaic virus (CaMV) 19S and 35S and the figwort mosaic virus 35S-promoters, the maize adh1 promoter, the light-inducible promoter from the small subunit of ribulose-1,5-bis-phosphate carboxylase (ssRUBISCO, a very abundant plant polypeptide), and the chlorophyll a/b binding protein gene promoter, and a cryptic promoter (tCUP) from tobacco. All of these promoters have been used to create various types of DNA constructs which have been expressed in plants. Preferred promoters include: the actin promoter, a constitutive promoter from rice (McElroy et al., 1990); Ubi-1, a constitutive promoter functional in many monocots (Wan and Lemaux, 1994); Hordein B1, a seed specific promoter from barley (Knudsen and Müller, 1991); HMW glutelin (Lee et al., 1991), a tissue-specific promoter from wheat; and α-*amy-I*, a tissue-specific promoter from wheat (Jacobsen and Close, 1991).

In addition to a promoter sequence, the expression cassette should also contain a transcription termination region downstream of the structural gene to provide for efficient termination. The termination region may be obtained from the same gene as the promoter sequence or may be obtained from different genes. A useful transcription termination region is the nopaline synthase NOS 3' terminator sequence (Bevan et al. 1983).

Polyadenylation is believed to have an effect on stabilizing mRNAs. Therefore, polyadenylation sequences are also commonly added to the vector construct if the mRNA encoded by the structural gene is to be efficiently translated (Alber and Kawasaki, 1982). Polyadenylation sequences include, but are not limited to the *Agrobacterium* octopine synthase signal (Gielen et al., 1984) or the nopaline synthase signal (Depicker et al., 1982). The vector will also typically contain a selectable marker gene by which transformed plant cells can be identified in culture. Numerous selectable marker genes are known in the art and are readily available. Typically, the marker gene encodes antibiotic resistance or herbicide resistance. These markers include those that confer resistance to the antibiotics ampicillin (the amp gene), kanamycin (the nptil gene), chloramphenicol (the cat gene), G418, hygromycin, bleomycin, kanamycin, and gentamycin. Other markers confer resistance to herbicides, such as the bar gene, which confers resistance to glufosinate ammonium, the active ingredient of the herbicides BIOLAPHOS™, BASTA™ and LIBERTY™. Those cells containing the vector will be identified by their ability to grow in a medium containing the particular selective agent.

The vector may also contain a reporter gene for the analysis of plant gene expression. A suitable reporter gene is the bacterial gene uidA, encoding β-glucuronidase (GUS). GUS expression can be conveniently quantified through a highly sensitive non-radioactive assay using the fluorogenic substrate 4-methylumbelliferyl glucuronide (MUG) (Spoerlein et al., 1991). Other suitable reporter genes include those encoding beta-galactosidase, luciferase, and chloramphenicol acyltransferase.

Once an appropriate vector has been assembled, a variety of techniques are available for introducing the vector into the monocotyledonous plant cells (Potrykus, 1990). Although *Agrobacterium*-mediated transformation is used principally in dicot species, recent evidence suggests that monocots could be transformed with hypervirulent *Agrobacterium* strains (Creissen et al., 1990). DNA may also be transferred to monocot protoplasts either by electroporation (Fromm et al., 1986) or through the use of polyethylene glycol (PEG) (Paszkowski et al. 1984). Alternatively, the vector can be micro-injected directly into plant cells (Toyoda et al., 1990) or introduced into cells electrophoretically (Ahokas, 1989). Other approaches to transforming plant cells include fusion of cereal protoplasts with cationic liposomes containing DNA (Antonelli and Stadler, 1990), penetration of the cell wall with a laser beam (Kaneko et al., 1991), and dry seed imbibition in DNA solution (Töpfer et al., 1989).

In accordance with the invention, particle bombardment (Weeks et al., 1993; Wan and Lemaux, 1994; Cho et al., 1998) is a preferred method for introducing the vector into the monocotyledonous plant cells. In this technique, DNA coated microcarriers are accelerated to high velocity by a particle gun apparatus. Due to acceleration, the microcarriers cross the cell wall/membrane barrier, deliver the foreign DNA inside the cell, and the transformants are regenerated under selection. The microcarriers should be of sufficient mass to possess adequate momentum to penetrate the appropriate tissue. Suitable metal particles include gold, tungsten, palladium, rhodium, platinum, iridium and perhaps other second and third row transition metals. Metals should be chemically inert to prevent adverse reactions with the DNA or cell components The particles may be selected for size and shape, as well as agglomeration and dispersion properties, as are known in the art. Certain additives such as spermidine and calcium chloride may be beneficially added to the DNA coated onto the microcarriers. Suitable particle gun apparatus is known in the art and is readily available, such as the Helios Gene Gun System (Bio-Rad, Hercules, Calif.) which is suitable. Baffles or mesh screens may be used to reduce physical trauma to cells from the gas blast and acoustic shock generated by the particle gun, resulting in reduced cell death and increased transformation efficiency.

Transformation of plant cells, particularly by particle bombardment or *Agrobacterium*-mediated transformation, is preferably conducted prior to development of the primary embryo under conditions conducive to direct somatic embryogenesis, but may occur anywhere from about zero to five days after commencement of tissue culture. Prior to transformation, the culture medium does not contain a selective agent. Approximately 16 hours after transformation, the cells are preferably transferred to media supplemented with the appropriate selective agent. For instance, if the marker gene used is the bar gene, an appropriate selective agent is glufosinate ammonium. The selective agent preferably is present during each of the subsequent tissue culture and regeneration steps. If the step of direct somatic embryogenesis is not included, transformation of callus cells, suspension cells, or microspore-derived embryos may be effected prior to culturing on SEM medium.

After transformation, transformed plant cells or plants carrying the introduced DNA are identified, typically by selection for a marker gene and/or a reporter gene, as described previously.

In an exemplified case, barley cells transformed with the bar marker gene were selected by growing the cells on growth medium containing glufosinate ammonium. Only successfully transformed cells that were resistant to the herbicide survived. The presence of the uidA reporter gene in the surviving cells was detected by the observation of blue dots on one of the regenerated plants, indicative of β-glucuronidase (GUS) activity.

Alternatively, expression of the foreign DNA can be confirmed by detection of RNA encoded by the inserted DNA using well known methods such as Northern blot hybridization. The inserted DNA sequence can itself be identified by Southern blot hybridization or the polymerase chain reaction (PCR) (Sambrook et al., 1989; Ausubel et al., 2000). In Examples 5 and 6 herein, the presence of the bar and uidA genes was confirmed by PCR amplification and Southern blot hybridization (Tables 7 and 8).

Recombinant DNA procedures and tissue culture procedures used for practicing the invention and which are not described in detail herein involve standard laboratory techniques as described in Sambrook et al. (1989), Ausubel et al. (2000), or Zrÿd and Richards (1988).

Generally, enzymatic reactions involving DNA ligase, DNA polymerase, restriction endonucleases and the like are performed according to the manufacturer's specifications. Abbreviations and nomenclature employed herein are standard in the art and are commonly used in scientific publications such as those cited herein.

The invention is further illustrated by the following non-limiting Examples.

EXAMPLE 1

Direct Somatic Embryogenesis, Secondary Embryogenesis and Regeneration of Barley Genotypes i) Explant Source Immature embryos of seven barley genotypes, as described in Table 3 herein, were used for this study, including Canadian six-row forage lines, two-row feed barley varieties and the two-row malting barley cultivar Golden Promise. Golden Promise is used extensively as a model cultivar for barley because of its ability to regenerate relatively well with in vitro culture protocols (Bregitzer et al., 1998).

Stock plants were grown in growth chambers with 16-h photoperiod (bottom/top of plants: 270/330 $\mu$mol m$^{-2}$ s$^{-1}$) with 21/16° C. day/night temperature regimes. Immature spikes were harvested around 14 days post-anthesis. At this developmental stage, the embryos varied from 1.5 to 2 mm in size. Spikes were collected and kept in a refrigerator at 4° C. for three to seven days for a cold pre-treatment. Immature caryopses were collected and then washed for 30 s with 70% ethanol, and surface sterilized in 10% bleach for 10 min in a laminar flow hood. Then, three washes with double distilled sterilized water were applied for 1 min each.

Dissection of the caryopses was carried out under a stereo-microscope, using forceps and a modified scalpel blade (shaped over a burner to form a hook having a radius of curvature to match the outer surface of the germ to be extracted) to dissect the immature seed. The caryopsis was held with the forceps, and the seed coat above the immature embryo was removed with the blade. The exposed germ was then cut out, and the scutellum gently removed from the caryopsis with the smooth side of the blade. The scutellum was placed up-side-down on the first medium, DSEM (Table 2). This approach minimized physical damage to the scutella, ensured that all germ tissues were removed, and accelerated the isolation of scutella.

ii) Immature Scutella Culture

Excised scutella were grown in the dark at 25° C. on DSEM medium (composition of all media is reported in Table 2), until primary embryos located on the top of scutella were developed to the globular developmental stage. Tissues were examined under a stereo-microscope to determine the developmental stage. Tissues at the globular developmental stage were transferred to the SEM medium, and cultivated in the dark at 25° C. until secondary embryogenesis could be detected using a stereo-microscope. Then, tissues carrying primary and secondary embryos were cut into two to four pieces and transferred to GEM medium. Most of the embryos grew, and some could germinate on GEM medium. When two or more secondary embryos were attached to a primary embryo, these tissues were preferably cut again, before putting them in the regeneration medium MS$_{reg}$, under light (80 $\mu$molm$^{-2}$ s$^{-1}$) at 16° C. To further increase the number of regenerated plants, all primary embryos were systematically cut to favor the germination of all secondary embryos. Green embryos that germinated on the regeneration medium were removed and transferred to a rooting medium in Magenta boxes, under the same light conditions, which allowed plantlets to develop their roots.

iii) Experimental Method

Twenty scutella were randomly plated in each petri dish. Each genotype was represented by three dishes containing 20 scutella each. For each experimental unit, the number of scutella that produced plantlets and the total number of plantlets were recorded. A "plantlet" was defined as a small regenerated plant with green shoots and roots that arose from either germinating primary or secondary embryos. Mean and standard deviation for the mean were calculated for each genotype.

iv) Results

The same developmental pattern for direct somatic embryogenesis was observed on scutella of the seven barley genotypes representing forage, feed and malting barley. Direct somatic embryogenesis up to the globular stage was induced by the DSEM medium. Globular embryos were observed on most scutella. Two forage type barley lines, H84108005NX and H8902001N, produced as many direct somatic embryos as Golden Promise, a non-recalcitrant barley cultivar for tissue culture (Table 3). Secondary embryogenesis was induced by the SEM medium from the primary globular embryos for all genotypes tested. The secondary embryos always developed from the primary globular embryos, which sometimes started to germinate on the SEM medium. Further development of the primary embryos occurred in the GEM medium when the number of embryos were low. It appeared that the withdrawal of cytokinin partially enabled the larger primary embryos to inhibit the growth of the younger secondary embryos, which is similar to the apical dominance observed in adult plants. Cutting scutella to allow primary embryos to develop freely was beneficial, but it was not possible without damaging the primary embryos. On average, 50 plantlets from germinating primary and secondary embryos were regenerated from the initial 20 scutella. Forage and feed barley cultivars had been previously identified as recalcitrant to in vitro culture regeneration. All lines but one yielded numbers of plantlets similar to Golden Promise (Table 3). The number of plants regenerated was impressive despite the fact that the quality of the stock plants used for isolating the scutella were poor due to disease infection. Stress generally reduced the ability of plants to regenerate in vitro. A preferred method to further increase the number of regenerated plants would be to systematically cut all primary embryos to favor the development and germination of all secondary embryos. These results are also believed to represent the first report of direct somatic embryogenesis and secondary embryogenesis in monocots.

EXAMPLE 2

Direct Somatic Embryogenesis and Secondary Embryogenesis from Scutella of Barley, Wheat and Durum Wheat Amphiploids i) Immature Scutella Culture The tissue culture protocols and experimental unit for barley and wheat were essentially the same, and were similar to that described in Example 1. The barley and wheat embryos were 2 mm in size. Tissues were grown in the DSEM medium until the primary embryos on top of scutella were at the globular stage, and then scutella were cut into two pieces.

ii) Results

A very large number of primary and secondary embryos were produced during this experiment. Therefore, only the number of plantlets which germinated from either primary or secondary embryos was recorded (Table 4). Scutella from all barley genotypes followed the sequence of direct somatic embryogenesis, secondary embryogenesis, germination, regeneration and rooting, as in Example 1. The step of growing the embryos on rooting medium was not necessary for the wheat cultivars, because they produced roots easily on the regeneration medium $MS_{reg}$. One group of genotypes, AC Nanda, AC Fielder, T89037005X, AC Lacombe, Golden Promise and T89047103NX, produced between six and ten primary globular embryos per scutellum. The three other genotypes, T89034001, Harrington and H84107004N, produced about three primary globular embryos per scutellum. Once primary globular embryos were well developed, no differences were observed among genotypes in the numbers of secondary embryos produced.

The secondary embryos were more compact in barley (FIGS. 1 and 2) than in wheat in which they arise as distinct bulges (FIG. 3), making identification of barley secondary embryos more difficult. Wheat secondary embryos developed individually in the equatorial plane of the primary globular embryo (FIG. 3). They were very similar to the zygotic embryos.

Non-stressed plants were used in this experiment, and scutella were similar in size. A uniform response from scutella and a higher number of primary globular embryos were observed in this experiment compared to the results reported in Example 1 (Table 3). Fully developed primary globular embryos responded very well to SEM medium as they produced between one and ten secondary embryos. Preferably, primary globular embryo are fully developed on the DSEM medium in order to get a maximum induction of secondary embryos on the second medium. The scutella were cut in pieces to allow primary embryos to develop freely and to ensure successful germination. However, it was not possible to detach the secondary embryos from the primary embryos without damaging them.

These results showed that the invention is capable of inducing direct somatic embryogenesis and secondary embryogenesis in a wide range of barley and wheat genotypes. The results also demonstrate that direct somatic embryogenesis reduces the number of days required to regenerate plants using in vitro culture, the methods of the invention providing green, fertile barley plants about two months earlier than the typical callus induction and regeneration approach, and green, fertile wheat plants about one month earlier than the best callus induction and regeneration approach. The forage, feed and some malting barley cultivars used in these experiments were previously considered recalcitrant to in vitro regeneration. These results are also believed to represent the first report of direct somatic embryogenesis and secondary embryogenesis in monocots.

Similar results were obtained from the interspecific cross *Triticum durum* cv Calvin/*Elytrigia disticha*//Calvin, $BC_1F_5$. *Elytrigia disticha* is a grass and a wild relative of wheat. Many disease resistance genes from wild and related grasses have been introduced to wheat. Ten scutella were excised and treated as above. After seven days of culture on the DSEM medium, fully developed primary globular embryos were identified. After another 11 days in SEM medium, secondary embryogenesis was completed. From the 10 scutella originally plated, 120 plantlets (1200%) were regenerated. These results demonstrate that direct somatic embryogenesis can be used with different species of wheat, *Triticum durum*, and their wild grass relatives.

EXAMPLE 3

Direct Somatic Embryogenesis, Secondary Embryogenesis and Regeneration of Oat, Rye Wheat, Barley, Durum Wheat, *Triticum monococum* and *Triticum urartu* i) Explant Source

Immature embryos of oat, rye, wheat, barley, durum wheat, *T monococum* and *T. urartu*, as described in Table 5 herein, were used for this study, including the lines of Juniper and CDC Pacer in oat; perennial cereal rye (PC Rye); Hy366-BL31 and P8810-B5B3A2A2 in common wheat; DT701 in durum wheat; accessions 89, 173, 238 in *T. monococum*; accession 17111 in *T. urartu*; Golden Promise and T89047103NX in barley.

Scutella were isolated from the immature embryos as described in Example 1. Briefly, caryopses containing immature embryos at 15 days post-anthesis were dissected. At this developmental stage, the embryos were about 2 mm in length for all species, except those of *T. monococum* and *T. urartu* which were 1.5 mm in length.

ii) Immature Scutella Culture

Excised scutella were placed upside-down on the DSEM medium and grown, until the primary embryos located on top of the scutella reached the globular stage. Direct somatic embryogenesis along the scutellum was observed in all species, with the exception of oat in which direct somatic embryogenesis was observed only at one extremity of the scutellum, while all other parts of the scutellum turned brown and died in a few days. Scutella carrying primary embryos at the globular stage were cut into pieces to separate the primary embryos which were then transferred to SEM medium, on which most of the primary embryos grew, with some germinating early.

iii) Experimental Method

Twenty scutella were randomly plated in each petri dish. Each genotype was represented by three dishes containing 20 scutella each. For each experimental unit, the number of scutella that produced plantlets and the total number of plantlets were recorded. A "plantlet" was observed as a small regenerated plant with green shoots and roots that arose from either germinating primary or secondary embryos.

iv) Results

Most of the genotypes showed a high embryogenic response, while only CDC Pacer (oat) showed a low response. Green and fertile plantlets were regenerated from all genotypes (Table 5). The regeneration was very high in common wheat and barley. A very good level of regeneration was observed for the diploid wheat species *T. monococum* and *T. urartu*, durum wheat and oat.

Regeneration was more modest for one cultivar of oat and the perennial cereal rye. However, regeneration in these species is intriguing, since they are characterized by cross-fertilization and large variation in the temporal developmental stage of embryos. Since an oat panicle has caryopses that vary in age, it was thus more difficult to collect embryos of the same age, and to obtain enough embryos with a suitable size in the same day. Furthermore, under stress, oat embryos produce phenolic compounds that are toxic to the embryo itself. Durum wheat regeneration is significant, in that this species has been recognized as recalcitrant for regeneration. *T. monococum* is also very recalcitrant, although regenerated plantlets were obtained at a high frequency despite the smaller size of the embryo in this diploid wheat. These results are believed to represent the first report of regeneration of the wheat diploid species *T. urartu*.

All genotypes from seven different species were thus regenerated, with common wheat and Golden Promise (barley) showing the highest response, most likely since this novel method was originally designed for barley and common wheat, and the selected size of the scutellum was optimum for such species. Further, the regeneration of these seven species demonstrates that the method is effective for different species, even those (e.g. oat, *Triticum monococum* and *T. urartu*) which have been previously recognized to be recalcitrant to in vitro regeneration, and successfully induces direct somatic embryogenesis and secondary embryogenesis in a wide range of monocotyledonous species. These results are also believed to represent the first report of successful direct somatic embryogenesis and secondary embryogenesis in these seven species of monocots.

EXAMPLE 4

Direct Somatic Embryogenesis from Immature Scutella of Sorghum and Corn Followed by Organogenesis.

i) Explant Source

Immature embryos of sorghum and corn as described in Table 6 herein, were used for this study, including the lines of CK60 and PI229828 in sorghum and H96F and HFDM in corn. Scutella were isolated from the immature embryos as described in Example 1. Briefly, caryopses containing immature embryos at 15 days post-anthesis were dissected. At this developmental stage, the embryos were approximately 2 mm in length.

ii) Immature Scutella Culture

Excised scutella were placed upside-down on the DSEM medium and grown, until the primary embryos located on top of the scutella reached the globular stage. Direct somatic embryogenesis along the scutella was observed in both sorghum and corn. Scutella carrying primary embryos at the globular stage were cut in two pieces to separate groups of primary embryos which were then transferred to SEM medium, on which most of the primary embryos grew.

iii) Experimental Method

Twenty scutella were randomly plated in each petri dish. Each genotype was represented by one dish containing 20 scutella each. For each experimental unit, the number of scutella that produced plantlets and the total number of plantlets were recorded. A "plantlet" was observed as a small regenerated plant with green shoots and roots.

iv) Results

For sorghum, a very large number of primary embryos on DSEM and new shoots on SEM (organogenesis) developed during this experiment; thus, only the number of regenerated plantlets were recorded (Table 6). Sorghum scutella reacted rapidly to the stresses of dissection and in vitro culture. Frequently, one section of the scutellum turned brown and died, while the other carried many globular embryos. A few albino plantlets were regenerated from genotype PI229828, replicate 1, but are not counted in Table 6.

Corn produced fewer primary embryos on DSEM and consequently fewer new shoots on SEM than sorghum.

Scutella from all sorghum and corn genotypes followed the sequence comprising direct somatic embryogenesis (on DSEM), early germination (on SEM), initiation of organogenesis (on SEM), regeneration (on GEM and MS regeneration) and rooting (on rooting medium). Organogenesis, the formation of new shoots, occurred on the stems of early germinated primary embryos. The origin of these shoots is thus very different from that of secondary embryos, which originate at the equatorial plane of primary wheat globular embryos.

These results demonstrate that this novel method is suitable to induce direct somatic embryogenesis and organogenesis for sorghum and corn genotypes. These results are also believed to represent the first report of this combination of developmental patterns in monocots.

EXAMPLE 5

Figure 4:
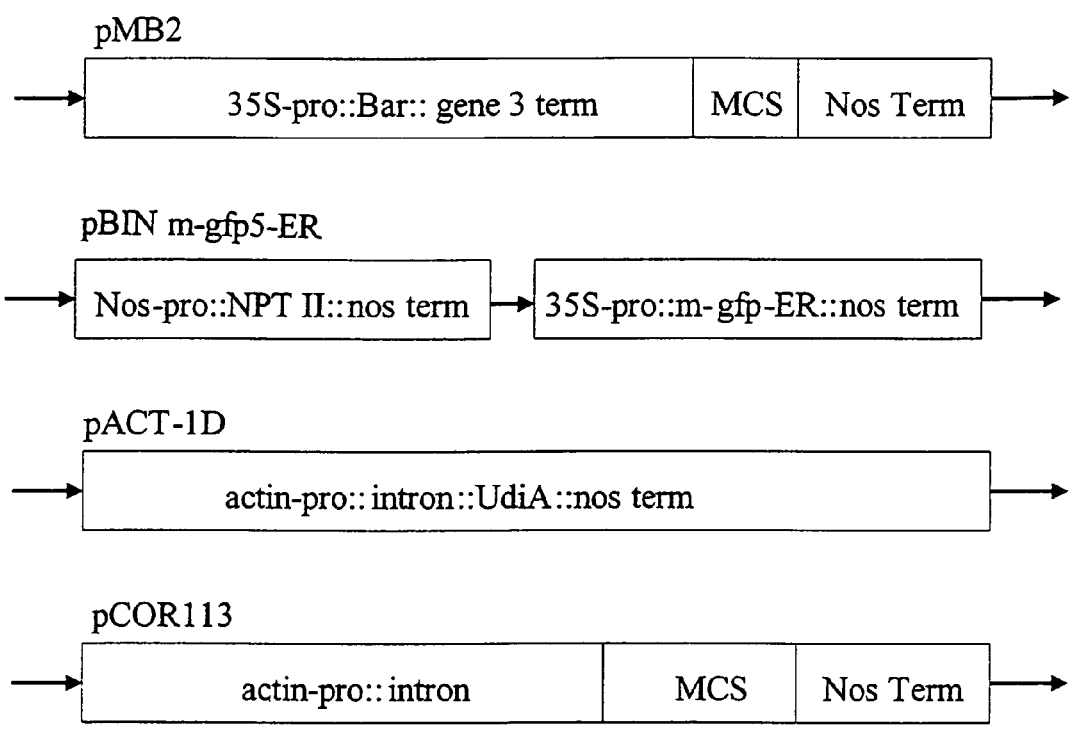
FIG. 4 illustrates various gene constructs used in the Examples herein.

Biolistic Transformation of Barley with the bar and uidA Genes i) Co-transformation DNA delivery to the tissues was carried out with the Helios Gene Gun System, a microprojectile bombardment device from Bio-Rad (#165-2431, 2000 Alfred Nobel Drive Hercules, Calif. USA 94547). The plasmid pMB2 (Steve Holzberg, Berkeley University Albany Calif. 94710), carrying the marker gene bar (FIG. 4), and the plasmid pACT-1D (Ray Wu, Cornell University), carrying the reporter gene uidA (FIG. 4), were used. Equal amounts of these two plasmids (25 μg each) were mixed and coated on 25 mg of 1 μm gold particles and distributed on the inside wall of a 60-cm GoldCoat tube according to the manufacturer's instructions. Discharge pressure was set at 120–140 psi and a diffusion screen (#165-2475) was used to ensure an even distribution of the gold particles carrying the plasmids.

The tissue culture protocol was essentially the same as that described in Example 2. Barley scutella were bombarded after two days of culture in the DSEM medium. Twenty scutella were transferred onto a modified DSEM medium supplemented with 0.3M mannitol, from 4 h before bombardment to 16 h after bombardment. Forty scutella of Golden Promise, 40 scutella of H89108005NX, and 20 scutella of Seebe were bombarded with plasmid-coated gold particles.

ii) Regeneration of Glufosinate-tolerant Plants

The scutella were transferred to the DSEM medium containing 5 mg/L of glufosinate ammonium salt (#C140300, Crescent Chemical, Hauppauge N.Y. USA), 16h after bombardment. All other steps of tissue culture were accomplished with the selecting chemical at the above concentration. Embryogenesis was slightly delayed and less frequent during the selection procedure using the glufosinate, but there was no impact on the quality of primary and secondary embryos produced. Only a very few escapes (four plants out of 200) were observed from the tissues bombarded with empty gold particles and non-bombarded tissues. Growth of these negative control tissues was much slower and necrosis was frequent. This confirmed that the selection procedure using glufosinate was very effective to eliminate most of the non-transgenic plantlets.

At the regeneration step, cuttings were done where necessary to isolate tolerant germinating secondary embryos, or groups of secondary embryos, as glufosinate-sensitive germinating embryos turned yellow. Rooting medium was not supplemented with glufosinate ammonium salt. Herbicide-tolerant plantlets were recovered and transferred to potting mix within two to three months of initiation of direct embryogenesis. In contrast, previous methods take more than four months to regenerate recalcitrant genotypes such as Harrington (Cho et al., 1998).

iii) Characterization of Selected Green Plants

Herbicide-resistant regenerated plants were tested with the leaf brush technique (LBT) wherein glufosinate ammonium salt at a concentration of 500 mg/L was applied abundantly to leaves of the regenerated plants with a small paint brush. Polymerase chain reaction (PCR) product was probed to confirm presence of the bar DNA in the plant cells. PCR and Southern blot analyses were used to check reporter gene insertion. Marker (bar) and reporter (uidA) genes were detected in the regenerated plants (Table 7). From a total of 100 bombarded embryos of three genotypes, Golden Promise, H89108005NX and Seebe, nine fertile plants were regenerated. These plants subsequently produced seeds. All plants carried the bar gene, but two did not express a high tolerance to the glufosinate ammonium using the LBT assay. Five plants also carried the uidA gene, and blue dots resulting from the in vivo GUS activity were detected in one plant.

These results confirmed that the selection procedure eliminated the non-transgenic plantlets. The transformation protocol was very efficient with the tissue culture techniques of the invention. Regeneration rate of transgenic fertile plant reached 17% for Golden Promise and 5% for the forage barley H89108005NX. The co-transformation technique resulted in 50% reporter/marker gene insertion ratio for the cultivar/lines. Regeneration of transgenic lines from Seebe was not successful in this particular trial. This may have been due to the low number of scutella used for this cultivar.

EXAMPLE 6

Biolistic Transformation of Barley with bar and gfp Genes i) Co-transformation

DNA delivery to the tissues was carried out with the Helios Gene Gun System, described in Example 3 above. The plasmid pMB2 (Steve Holzberg, Berkeley University Albany Calif. 94710), carrying the marker gene bar (FIG. 4), and the plasmid pBIN m-gfp5-ER (Jim Haseloff, MRC Cambridge England CB2 2QH), carrying the reporter gene gfp (FIG. 4), were used. Equal amounts of these two plasmids (25 μg each) were mixed and coated on 25 mg of 1 μm gold particles and distributed on the inside wall of a 60-cm GoldCoat tube according to the manufacturer's instructions. Discharge pressure was set at 120–140 psi and a diffusion screen (#165-2475) was used to ensure an even distribution of the gold particles carrying the plasmids.

The tissue culture protocol was essentially the same as that described in Example 2. Barley scutella were bombarded after two days of culture on DSEM medium. Twenty scutella were transferred onto a modified DSEM medium supplemented with 0.3M mannitol, from 4 h before bombardment to 16 h after bombardment. A total of 320 scutella from seven genotypes were bombarded for this experiment.

ii) Regeneration of Glufosinate-Tolerant Plants

The scutella were transferred to DSEM medium containing 5 mg/L of glufosinate ammonium salt (#C140300, Crescent Chemical, Hauppauge N.Y. USA), 16 h after bombardment. The rest of the tissue culture steps were accomplished with this chemical at the same concentration. Embryogenesis was slightly delayed and less frequent during selection procedure using the glufosinate, but there was no impact on the quality of primary and secondary embryos produced.

At the regeneration step, cuttings were done where necessary to isolate tolerant germinating secondary embryos or groups of secondary embryos, as herbicide sensitive germinating embryos turned yellow and thus were easy to identify. Rooting medium was not supplemented with glufosinate ammonium salt. Herbicide-tolerant plantlets were recovered and transferred to potting mix within two to three months of test initiation. In contrast, previous methods take more than four months to regenerate recalcitrant genotypes such as Harrington (Cho et al., 1998).

iii) Characterization of Selected Green Plants

Herbicide-resistant regenerated plants were tested with the leaf brush technique as in the previous Example. PCR product was probed to confirm presence of the bar DNA into the plant cells. PCR and Southern blot technique were used to check reporter gene insertion. Marker (bar) and reporter (gfp) genes were detected in the regenerated plants (Table 8). From a total of 320 bombarded embryos of four genotypes, Golden Promise, H84012004, Harrington and Phenix, 30 fertile plants were regenerated and these subsequently produced seeds. Twenty-six plants carried the bar gene and 18 expressed a higher tolerance to the glufosinate ammonium. Eleven plants also carried the f gene.

The transformation protocol was very efficient with the tissue culture technique of the invention. Regeneration rates of transgenic fertile plant reached 21% for Golden Promise, 20% for genotype H84012004, 5% for Harrington and 2.5% for Phenix. Success of the co-transformation technique was similar to the expected reporter/marker gene insertion ratio of 50%.

EXAMPLE 7

Biolistic Transformation of Wheat with the bar Gene and a Candidate Yr10 Resistance Gene which Confers Yellow Stripe Rust Resistance i) Co-transformation DNA delivery to the tissues was carried out with the Helios Gene Gun System as described in the preceding Examples. The plasmid pCOR113 (Ray Wu, Cornell University) carrying the marker gene, bar, (FIG. 4) and a second vector pCOR113 carrying the candidate Yr10 resistance gene 4B (FIG. 4) were used. An equal mass of these two plasmids (25 µg each) was mixed and coated on 25 mg of 1 µm gold particles and distributed on the inside wall of a 60-cm GoldCoat tubing according to the manufacturer's instructions. Discharge pressure was set at 120–140 psi and a diffusion screen (#165-2475) was used to ensure an even distribution of the gold particles carrying the plasmids.

The tissue culture protocol was essentially the same as that described in Example 2. Wheat scutella were bombarded after two days of culture in DSEM medium. Twenty scutella were transferred onto a modified DSEM medium supplemented with 0.3M mannitol, from 4 h before bombardment to 16 h after bombardment. Forty scutella of the genotype AC Fielder were bombarded with the gold particles. AC Fielder is susceptible to most common races of pathogens causing the stripe rust disease.

ii) Regeneration of Glufosinate-Tolerant Plants

The scutella were transferred to DSEM medium containing 5 mg/L of glufosinate ammonium salt (#C140300, Crescent Chemical, Hauppauge N.Y. USA), 16 h after bombardment.

The further steps of tissue culture were accomplished with this selecting chemical at the same concentration. Embryogenesis was slightly delayed and less frequent during selection procedure using the glufosinate, but there was no impact on the quality of primary and secondary embryos produced.

At the regeneration step, cuttings were done where necessary to isolate tolerant germinating secondary embryos, or groups of secondary embryos, as herbicide sensitive germinating embryos turned yellow. Herbicide-tolerant plantlets were recovered and transferred to potting mix within only two to three months of initiation. In contrast, Becker et al. (1994), report a total time from beginning of culture until the transfer of putative transformed wheat plants to soil of between 15 and 17 weeks.

iii) Characterization of Selected Green Plants

Herbicide-resistant regenerated plants were tested with the leaf brush technique as in the previous Examples. PCR product was probed to confirm presence of the bar DNA in the plant cells. PCR and Southern blot analyses were used to check yellow stripe rust resistance gene insertion. A marker (bar) and the candidate Yr10 resistance gene were detected in regenerated plants. From a total of 40 bombarded scutella, 46 fertile plants were regenerated and produced seeds. Sixty three percent carried the bar gene. However, only eight expressed a very high tolerance to the glufosinate ammonium. Screening for yellow strip rust resistance was very efficient, as all plants but one were susceptible to the pathogen. The resistant plant expressed the characteristic hypersensitive response to the fungal attack. Once again, transformation protocol was very efficient with the tissue culture technique of the invention. The regeneration rate of transgenic plants expressing disease resistance was about 2.5%, which is at least 10 times higher than the expression rate of any heterologous gene in any other protocol currently available.

TABLE 2

Composition of the five tissue culture media used for induction and development of direct somatic embryogenesis of monocots (DSEM), secondary embryogenesis of monocots (SEM), germination of embryos of monocots (GEM) and rapid regeneration of normally developing green and fertile (MS$_{reg}$ and rooting media) cereal plants.[1]

| Composition | DSEM medium | SEM medium | GEM medium | MSreg medium | Rooting medium |
|---|---|---|---|---|---|
| Salts | mg/L | mg/L | mg/L | mg/L | mg/L |
| CaCl$_2$·2H$_2$O | 440.00 | 440.00 | 440.00 | 440.00 | 440.00 |
| MgSO$_4$·7H$_2$O | 370.00 | 370.00 | 370.00 | 370.00 | 370.00 |
| NH$_4$NO$_3$ | 165 | 165.00 | 165.00 | 1,650.00 | 1,650.00 |
| KH$_2$PO$_4$ | 170.00 | 170.00 | 170.00 | 170.00 | 170.00 |

TABLE 2-continued

Composition of the five tissue culture media used for induction and development of direct somatic embryogenesis of monocots (DSEM), secondary embryogenesis of monocots (SEM), germination of embryos of monocots (GEM) and rapid regeneration of normally developing green and fertile ($MS_{reg}$ and rooting media) cereal plants.[1]

| Composition | DSEM medium | SEM medium | GEM medium | MSreg medium | Rooting medium |
|---|---|---|---|---|---|
| $KNO_3$ | 1,900.00 | 1,900.00 | 1,900.00 | 1,900.00 | 1,900.00 |
| $MnSO_4.4H_2O$ | 22.00 | 22.00 | 22.00 | 22.00 | 22.00 |
| $CoCl_2.6H_2O$ | 0.03 | 0.03 | 0.03 | 0.03 | 0.03 |
| $H_3BO_3$ | 6.20 | 6.20 | 6.20 | 6.20 | 6.20 |
| $ZnSO_4.7H_2O$ | 8.60 | 8.60 | 8.60 | 8.60 | 8.60 |
| $CuSO_4.5H_2O$ | 0.03 | 0.03 | 0.03 | 0.03 | 0.03 |
| $NaMoO_4.2H_2O$ | 0.25 | 0.25 | 0.25 | 0.25 | 0.25 |
| KI | | | | 0.83 | 0.83 |
| $FeSO_4.7H_2O$ | 27.85 | 27.85 | 27.85 | 27.85 | 27.85 |
| $NaEDTA.2H_2O$ | 37.23 | 37.23 | 37.23 | 37.23 | 37.23 |
| Carbohydrates | mg/L | mg/L | mg/L | mg/L | mg/L |
| Maltose | 15,000.00 | 15,000.00 | 15,000.00 | 15,000.00 | |
| Sucrose | 5,000.00 | 5,000.00 | 5,000.00 | 5,000.00 | 10,000.00 |
| Xylose | 350.00 | 350.00 | 350.00 | | |
| Ribose | 350.00 | 350.00 | 350.00 | | |
| Myo-inositol | 200 | 200 | 200 | 250 | |
| Amino acids | mg/L | mg/L | mg/L | mg/L | mg/L |
| Mix Amino Acid (U2.5)[2] | 337.00 | 337.00 | 337.00 | | |
| L-Glutamine | 750.00 | 750.00 | 750.00 | | |
| Glycine | | | | 2.00 | |
| Plant Growth Regulators | $\mu M$ | $\mu M$ | $\mu M$ | $\mu M$ | $\mu M$ |
| Spermine | 4.9 | 4.9 | 4.9 | | |
| Spermidine | 27.5 | 27.5 | 27.5 | | |
| 2,4-d | 7.9 | | | | |
| PAA | 22 | 11 | | 3.6 | 3.6 |
| BAP | 2.2 | 111 | | 0.4 | |
| Vitamins | mg/L | mg/L | mg/L | mg/L | mg/L |
| Pyridoxine.HCl | 1.00 | 1.00 | 1.00 | 1.00 | |
| Thiamine.HGl | 1.00 | 1.00 | 1.00 | 1.00 | |
| Pantothenate | 0.50 | 0.50 | 0.50 | 0.50 | |
| Nicotinic acid | 1.00 | 1.00 | 1.00 | 1.00 | |
| Riboflavin | 0.20 | 0.20 | 0.20 | 0.20 | |
| Folic acid | 0.20 | 0.20 | 0.20 | 0.20 | |
| Biotin | 0.20 | 0.20 | 0.20 | 0.20 | |
| Betaine chloride | 7.90 | 7.90 | 7.90 | 7.90 | |
| Choline.HCl | 10.00 | 10.00 | 10.00 | 10.00 | |
| Ascorbic acid | 0.40 | 0.40 | 0.40 | 0.40 | |
| Organic acids | mg/L | mg/L | mg/L | mg/L | mg/L |
| Malic acid | 1,000.00 | 1,000.00 | 1,000.00 | | |
| Fumaric acid | 200.00 | 200.00 | 200.00 | | |
| Succinic acid | 20.00 | 20.00 | 20.00 | | |
| a-Ketoglutaric acid | 20.00 | 20.00 | 20.00 | | |
| Citric acid | 5.00 | 5.00 | 5.00 | | |
| Pyruvic acid | 5.00 | 5.00 | 5.00 | | |
| Agar purified | | | | | 6,000.00 |
| Gelrite | 3,000.00 | 3,000.00 | 3,000.00 | 3,000.00 | |
| pH | 5.80 | 5.80 | 5.80 | 5.80 | 6.00 |

[1]Macro-salts and micro-salts composition is identical to MS medium, except for the first three media which have a 10 × reduction in NH4NO3 concentration.
[2]Sigma-Aldrich (Cat. # U-7756). The amino acid composition is L-asparagine, 60 mg/L; arginine, 30 mg/L; g-amino butyric acid, 80 mg/L serine, 55 mg/L; alanine, 30 mg/L; cysteine, 10 mg/L; leucine, 10 mg/L; iso-leucine, 10 mg/L; proline, 10 mg/L; lysine, 10 mg/L; phenylalanine, 5 mg/L; tryptophan, 5 mg/L; methionine, 5 mg/L; valine, 5 mg/L; glycine, 2.5 mg/L; histidine, 2.5 mg/L; threonine, 2.5 mg/L.

TABLE 3

Mean numbers (standard deviation) of responding scutella and number of regenerated plantlets originating from germinating primary and secondary embryos.

| Barley Genotypes | | Number of scutella producing germinating primary embryos per plate (max = 20) | Number of plantlets produced per plate* |
|---|---|---|---|
| H8902001N | 6-row forage | 18.3 (0.6) | 64.7 (10.0) |
| T89043003NX | 6-row forage | 8.0 (2.8) | 25.5 (4.9) |
| H84108005NX | 6-row forage | 16.3 (2.1) | 61.0 (5.0) |
| T89034001 | 6-row forage | 8.0 (1.0) | 43.0 (16.4) |
| Phenix | 2-row feed | 12.3 (1.5) | 53.3 (12.0) |
| Seebe | 2-row feed | 12 (1.7) | 45.0 (7.5) |
| Golden Promise | 2-row malting | 16.3 (1.1) | 57.0 (4.0) |
| Mean (STDEV) | | 13.0 (4.1) | 49.9 (13.4) |

*a group of closely germinating embryos was not separated and was further counted as a single plant.

TABLE 4

Mean number of regenerated plantlets and days of culture on media. A plantlet may originate from germinating primary and secondary embryos.

| Barley and Wheat Genotypes | replicate * | Days on DSEM | Days on SEM | Number of days to regenerate ** | Total plantlets | % *** |
|---|---|---|---|---|---|---|
| AC Nanda | 1 | 6 | 8 | 28 | 157 | |
| (Triticum aestivum) | 2 | 6 | 8–15 | 28–35 | 187 | |
| Soft white spring | 3 | 6 | 8–15 | 28–35 | 176 | |
| wheat | 4 | 8 | 20 | 42 | 144 | |
| | | 6–8 | 8–20 | 28–42 | 664 | 830 |
| AC Fielder | 1 | 6 | 6–10 | 26–36 | 174 | |
| (T. aestivum) | 2 | 6 | 6–10 | 26–36 | 162 | |
| Soft white spring | 3 | 6 | 9–23 | 29–42 | 206 | |
| wheat | 4 | 5 | 9–23 | 29–42 | 157 | |
| | | 5–6 | 6–23 | 26–42 | 699 | 874 |
| Golden Promise | 1 | 6–13 | 12–13 | 32–40 | 83 | |
| (Hordeum vulgare) | 2 | 9 | 19 | 42 | 163 | |
| 2-row malting | 3 | 9 | 19 | 42 | 174 | |
| | | 6–13 | 12–19 | 32–42 | 420 | 700 |
| T89034001 | 1 | 8 | 6–29 | 28–51 | 101 | |
| (H vulgare) | 2 | 8 | 6–29 | 28–51 | 69 | |
| 6-row forage | 3 | 8 | 6–29 | 28–51 | 112 | |
| | 4 | 5–10 | 7–32 | 26–56 | 23 | |
| | 5 | 5–10 | 2–28 | 21–56 | 46 | |
| | | 5–10 | 2–32 | 21–56 | 351 | 351 |
| H84107004N | 1 | 6 | 8 | 28 | 56 | |
| (H. vulgare) | 2 | 6 | 8–33 | 28–53 | 57 | |
| 6-row forage | 3 | 6 | 8–27 | 28–47 | 28 | |
| | 4 | 5–11 | 4–34 | 23–59 | 62 | |
| | 5 | 5 | 6–34 | 25–53 | 95 | |
| | | 5–11 | 4–34 | 23–59 | 298 | 298 |
| Harrington | 1 | 6–15 | 7–16 | 27–45 | 97 | |
| (H. vulgare) | 2 | 5–16 | 6–16 | 25–46 | 30 | |
| 2-row malting | 3 | 6 | 9–16 | 29–36 | 41 | |
| | 4 | 6–13 | 12–19 | 32–46 | 100 | |
| | | 5–16 | 6–19 | 25–46 | 268 | 335 |
| T89037005X | 1 | 7 | 6–29 | 27–50 | 218 | |
| (H. vulgare) | 2 | 7 | 6–29 | 27–50 | 178 | |
| 6-row forage | 3 | 5 | 6–10 | 25–29 | 197 | |
| | 4 | 5 | 6–10 | 25–29 | 257 | |
| | | 5–7 | 6–29 | 25–50 | 850 | 1062 |
| AC Lacombe | 1 | 7–17 | 6–29 | 27–60 | 197 | |
| (H. vulgare) | 2 | 7 | 6–29 | 27–50 | 210 | |
| 6-row feed | 3 | 5 | 6–27 | 25–46 | 121 | |
| | 4 | 5–10 | 7–28 | 26–52 | 106 | |
| | | 5–17 | 6–29 | 25–60 | 634 | 793 |
| T89047103NX | 1 | 6 | 6–29 | 26–49 | 151 | |
| (H. vulgare) | 2 | 6 | 6–29 | 26–49 | 128 | |

TABLE 4-continued

Mean number of regenerated plantlets and days of culture on media. A plantlet may originate from germinating primary and secondary embryos.

| Barley and Wheat Genotypes | replicate * | Days on DSEM | Days on SEM | Number of days to regenerate ** | Total plantlets | % *** |
|---|---|---|---|---|---|---|
| 6-row feed | 3 | 12<br>6–12 | 19<br>6–29 | 45<br>26–49 | 86<br>365 | 608 |

\* 20 scutella per plate
\*\* excludes number of days for rooting which was between 3 and 10 days for barley and 0 to 3 for wheat.
\*\*\* % of plantlets recovered relative to the original number of scutella cultured.

TABLE 5

Number of regenerated plantlets produced per genotype and percentage of plantlet regeneration per genotype among seven different species of monocots using primary and secondary embryogenesis.

| Species | Lines | Number of scutella | Number of regenerated plantlets | Percentage of regenerated plantlets |
|---|---|---|---|---|
| Triticum aestivum | HY366-BL31 | 40 | 754 | 1885 |
| Triticum aestivum | P8810-B5B3A2A2 | 20 | 372 | 1860 |
| T. durum | DT701 | 40 | 150 | 375 |
| T. monococum | 173 | 60 | 63 | 105 |
| T. monococum | 238 | 40 | 168 | 420 |
| T. monococum | 89 | 40 | 159 | 397 |
| T. urartu | 17111 | 29 | 49 | 170 |
| Hordeum vulgare | Golden Promise | 40 | 632 | 1580 |
| Hordeum vulgare | T89047103NX | 40 | 172 | 430 |
| Avena sativa | Juniper | 30 | 86 | 286 |
| Avena sativa | CDC Pacer | 20 | 5 | 25 |
| Secale cereale | PC Rye | 40 | 6 | 15 |

TABLE 6

Number of regenerated green plantlets and percentage of regenerated plantlets from sorghum and corn scutella from immature embryos through direct somatic embryogenesis followed by organogenesis.

| | Lines | Rep | Total number of day in culture | Number of regenerated plantlets | Percentage of regenerated plantlets |
|---|---|---|---|---|---|
| Sorghum | CK60 | 1 | 60 | 72 | 360 |
| | CK60 | 2 | 60 | 35 | 175 |
| | PI229828 | 1 | 70 | 101 | 505 |
| | PI229828 | 2 | 70 | 74 | 370 |
| Corn | H96F | 1 | 70 | 19 | 95 |
| | H96F | 2 | 70 | 25 | 125 |
| | HFDM | 1 | 70 | 30 | 150 |
| | HFDM | 2 | 70 | 22 | 110 |

TABLE 7

Characterization of nine individual regenerated barley plants ($T_0$) transformed with the bar and uidA genes.

| | | Marker (bar) | | Reporter (uidA) | | |
|---|---|---|---|---|---|---|
| # | Genotype | PCR | LBT | Probe PCR | GUS assay | Southern blot |
| 1 | Golden Promise | + | s | + | – | · |
| 2 | Golden Promise | + | r | – | – | – |
| 5 | Golden Promise | + | r | + | – | · |
| 6 | Golden Promise | + | r | – | – | · |
| 7 | Golden Promise | + | r | + | + | + |
| 8 | Golden Promise | + | r | – | – | – |
| 9 | Golden Promise | + | r | + | – | · |
| 3 | H89108005NX | + | s | – | – | – |
| 4 | H89108005NX | + | r | + | – | · |

PCR: polymerase chain amplification of either bar or uidA genes using specific primers
LBT: leaf brush technique to verify expression of the bar gene using a small paint brush to apply herbicide (500 mg/L glufosinate ammonium) to a leaf or portion thereof
GUS: b-glucuronidase activity
+: amplification of the specific DNA fragment, hybridization of probe to genomic DNA or positive enzymatic reaction
–: absence of amplification or hybridization or enzymatic activity
·: no data available
r: leaf resistant to herbicide application (no necrosis)
s: leaf susceptible to herbicide application (necrosis)

TABLE 8

Characterization of thirty individual regenerated barley plants ($T_0$) transformed with the bar and gfp genes.

| | | Marker (bar) | | Reporter (gfp) | |
|---|---|---|---|---|---|
| # | Genotype | PCR | LBT | Probe PCR | Southern blot |
| 35 | Golden Promise | + | r | – | · |
| 11 | Golden Promise | + | r | + | · |
| 12 | Golden Promise | + | s | – | – |
| 13 | Golden Promise | + | r | – | · |
| 14 | Golden Promise | + | r | – | · |
| 15 | Golden Promise | + | s | + | + |
| 16 | Golden Promise | + | r | + | – |
| 17 | Golden Promise | + | r | – | · |
| 18 | Golden Promise | + | r | – | · |
| 19 | Golden Promise | + | r | – | · |
| 21 | Golden Promise | + | s | + | · |
| 22 | Golden Promise | – | s | – | · |
| 23 | Golden Promise | – | s | – | · |
| 36 | Golden Promise | + | r | – | · |
| 37 | Golden Promise | – | r | + | + |
| 38 | Golden Promise | + | r | – | · |
| 46 | Golden Promise | + | r | + | · |
| 57 | Golden Promise | + | r | – | · |

TABLE 8-continued

Characterization of thirty individual regenerated barley plants (T$_0$) transformed with the bar and gfp genes.

| | | Marker (bar) | | Reporter (gfp) | |
|---|---|---|---|---|---|
| | | PCR | LBT | Probe PCR | Southern blot |
| # | Genotype | | | | |
| 58 | Golden Promise | + | s | − | . |
| *59 | Golden Promise | + | . | − | . |
| 10 | H84012004 | + | s | + | . |
| 39 | H84012004 | + | s | − | . |
| 40 | H84012004 | − | r | − | . |
| 41 | H84012004 | + | s | − | . |
| 42 | H84012004 | + | r | + | + |
| 24 | H89012004 | + | s | − | + |
| 25 | H89012004 | + | r | + | . |
| 26 | H89012004 | + | r | − | . |
| 27 | Harrington | + | r | + | . |
| 28 | Phenix | + | s | + | . |

*: plant died
PCR: polymerase chain amplification of either bar or uidA genes using specific primers
LBT: leaf brush technique to verify expression of the bar gene using a small paint brush to apply herbicide (500 mg/L glufosinate ammonium) to a leaf or portion thereof
+: amplification of the specific DNA fragment or hybridization of probe to genomic DNA
−: absence of amplification or hybridization or enzymatic activity
·: no data available
r: leaf resistant to herbicide application (no necrosis)
s: leaf susceptible to herbicide application (necrosis)

REFERENCES

Ahokas, H. (1989) Transfection of germinating barley seed electrophoretically with exogenous DNA. Theor. Appl. Genet. 77: 469.

Ahloowalia, B. S. (1982) Plant regeneration from callus culture in wheat. Crop Sci. 22: 405–410.

Alber, T. and Kawasaki, G. (1982) Nucleotide sequence of the triose phosphate isomerase gene of *Saccharomyces cerevisiae*. J. Mol. Appl. Gen. 1: 419–434.

Antonelli, N.M. and Stadler, J. (1990) Genomic DNA can be used with cationic methods for highly efficient transformation of maize protoplasts. Theor. Appl. Genet. 80: 395.

Arteca, R. (1996) Plant Growth Substances: Principles and Applications. New York. Chapman & Hall.

Ausubel, F. M., Bent, R., Kingston, R. E., Moore, D. J., Smith, J. A., Silverman, J. G. and Struhl, K. (2000) Current Protocols in Molecular Biology. John Wiley & Sons, New York.

Barcelo P., Hagel C., Becker, D., Martin, A. and Lorz H. (1993) Transgenic cereal (tritordeum) plants obtained at high efficiency by microprojectile bombardment of inflorescence tissue. Plant J. 5: 583–592.

Barro, F., Cannell, M. E., Lazzeri, P. A. and Barcelo, P. (1998) The influence of auxins on transformation of wheat and tritordeum and analysis of transgene integration patterns in transformants. Theor. Appl. Genet. 97: 684–695.

Becker, D., Brettschneider, R. and Lorz, H. (1994) Fertile transgenic wheat from microprojectile bombardment of scutellar tissue. Plant J. 5: 299–307.

Bevan, M. W., Flavell, R. B. and Chilton, M. D. (1983) A chimaeric antibiotic resistance gene as a selectable marker for plant cell transformation. Nature 304: 184–187.

Bhaskaran, S. and Smith, R. H. (1990) Regeneration in cereal tissue culture: a review. Crop Sci. 30 (6): 1328–1336.

Bregitzer, P., Dahleen, L. S. and Campbell, R. D. (1998) Enhancement of plant regeneration from embryogenic callus of commercial barley cultivars. Plant Cell Rep. 17: 941–945.

Burkhardt, P. K., Beyer, P., Wunn, J., Kloti, A., Armstrong, G. A., Schledz, M., Lintig, J. and Potrykus, I. (1997) Transgenic rice (*Oryza sativa*) endosperm expressing daffodil (*Narcissus pseudonarcissus*) phytoene synthase accumulates phytoene, a key intermediate of provitamin A biosynthesis. Plant J. 11: 1071–1078.

Carman, J. G. (1990) Embryogenic cells in plant tissue cultures: occurrence and behavior. In Vitro Cell Dev. Biol.:26: 746–753.

Cho, M. J., Jiang, W. I. and Lemaux, P. (1998) Transformation of recalcitrant barley cultivars through improvement of regenerability and decreased albinism. Plant Sci. 138: 229–244.

Creissen, G., Smith, C., Francis, R., Reynolds, H. and Mullineaux, P. (1990) *Agrobacterium*—and microprojectile—mediated viral DNA into barley microspore derived cultures. Plant Cell Rep. 8: 680.

De La Fuente, J. M., Ramirez-Rodriguez, V., Cabrera-Ponce, J. L. and Herrera-Estrella, L. (1997) Aluminum tolerance in transgenic plants by alteration of citrate synthesis. Science 276: 5466–1568.

Depicker, A., Strachel, S., Dhaese, P., Zambryski, P. and Goodman, H. M. (1982) Nopaline synthase: transcript mapping and DNA sequence *Agrobacterium tumefaciens*. J. Mol. Appl. Genet. 1(6): 561–573.

Dodeman, V. L., Ducreux, G. and Kreis M. (1997) Zygotic embryogenesis versus somatic embryogenesis. J. Exp. Bot. 48(313): 1493–1509.

Ducreux G., De Buyser J., Dodeman V., Haïcour R., Lavergne D., Nato A., Ouichou A., Picard E. and Sihachakr D., 1998. Recherches recentes et biotechnologies de la multiplication végétative. Cahiers Agriculture 7: 447–458.

Elliott, M. C., Moloney, M. M., Scott, N. W. and Slater, A. (1996) A way forward for tobacco—molecular farming. Biotech. and Biotechnol. Equip. 4: 59–66.

Fischer, R., Drossard, J., Commandeur, U., Schillberg, S. and Emans, N. (1999) Towards molecular farming in the future: moving from diagnostic protein and antibody production in microbes to plants. Biotech. and Appl. Biochem. 30(2): 101–108.

Fromm, M. E., Taylor, L. P. and Walbot, V. (1986) Stable transformation of maize after gene transfer by electroporation. Nature 319: 791.

Gamborg, O. L., Miller, R. A. and Ojima, K. (1968) Nutrient requirements of suspension cultures of soybean root cells. Exp. Cell Res. 50: 151–158.

George, E. F., Puttock, D. J. M. and George, H. L. (1987) Plant Culture Media Vol. 1, Formulations and Uses. Exegetics Limited.

Gielen, J., De Beuckeleer, M., Seurinck, J., Deboeck, F. and De Greve, H. (1984) The complete nucleotide sequence of the TL-DNA of the *Agrobacterium tumefaciens* plasmid pTiAch5. EMBO J. Eur. Mol. Biol. Organ. 3(4): 835–846.

Green C. E. (1982) Somatic embryogenesis and plant regeneration from the friable callus of *Zea mays*. In Plant Tissue Culture 1982: Proceedings, Fifth International Congress of Plant Tissue and Cell Culture. Fujiwara, A. Ed. Tokyo and Lake Yamanake, Japan, July 11–16. pp. 107–108.

Gruber, M. Y., Crosby, W. L., Glick, B. R. and Thompson, J. E. (1993) Vectors for Plant Transformation. In Methods in Plant Molecular Biology and Biotechnology. Glick, B. R. and Thompson, J. E. Eds. CRC Press, Inc. Boca Raton. pp. 89–119.

Hayashi, H., Alia., Mustardy, L., Deshnium, P., Ida, M. and Murata, N. (1997) Transformation of *Arabidopsis thaliana* with the coda gene for choline oxidase; accumulation of glycinebetaine and enhanced tolerance to salt and cold stress. Plant J. 12: 133–142.

Hemming, D. (1995) Molecular farming: using transgenic plants to produce novel proteins and other chemicals. AgBiotech News and Info. 7(1): 19–29.

Jacobsen, J. V. and Close, T. J. (1991) Control of transient expression of chimaeric genes by gibberellic acid and abscisic acid in protoplasts prepared from mature barley aleurone layers. Plant Mol. Biol. 16: 713.

Jähne, A., Becker, D. and Lörz, H. (1995) Genetic engineering of cereal crop plants: a review. Euphytica 85: 35–44.

Jähne, A., Becker, D., Brettschneider, R., and Lörz, H. (1994) Regeneration of transgenic, microspore-derived, fertile barley. Theor. Appl. Genet. 89: 525–533.

Kaneko, T., Kuroda, H., Hirota, N., Kishinami, I., Kimura, N. and Ito, K. (1991) Two transformation systems of barley—electroporation and laser perforation. In Barley Genetics VI. Vol. I. Munck, L., Kirkegaard, K and Jensen, B. Eds. Munksgaard, Copenhagen. p. 237.

Knudsen, S. and Müller, M. (1991) Transformation of the developing barley endosperm by particle bombardment. Planta. 185: 330.

Lee, B. T., Murdoch, K., Topping, J., Jones, M. G. K. and Kreis, M. (1991) Transient expression of foreign genes introduced into barley endosperm protoplasts by PEG-mediated transfer or into endosperm tissue by microprojectile bombardment. Plant. Sci. 78: 237–246.

Lee, J. H., Montagu, M. V. and Verbruggen, N. (1999) A highly conserved kinase in an essential component for stress tolerance in yeast and plant cells. Proc. Natl. Acad. Sci. USA 96: 5873–5877.

Lorz, H., Brettschneider, R., Hartke, S., Gill, R., Kranz, E., Langridge, P., Stolarz, A. and Lazzeri, P. (1990) In vitro manipulation of barley and other cereals. Stadler Genet. Symp. New York, N.Y. Plenum Press (19th). pp. 185–201.

Maeda E. and Thorpe T. A., 1979. Shoot histogenesis in tobacco callus cultures. In vitro 15: 415–424.

Maheswaran, G. and Williams, E.G. (1984) Direct somatic embryoid formation on immature embryos of *Trifolium repens, T. pratense* and *Medicago sativa*, and rapid clonal propagation of *T. repens*. Ann. Bot. 54: 201–211.

Maheswaran, G. and Williams, E. G. (1985) Origin and development of somatic embryoids formed directly on immature embryos of *Trifolium repens* in vitro. Ann. Bot. 56: 619–630.

Maheshwari, N., Rjyalakshmi, K., Baweja, K., Dhir, S. K., Chowdhry, C. N. and Maheshwari, S. C. (1995) In vitro culture of wheat and genetic transformation—retrospect and prospect. Crit. Rev. in Plant Sci. 14(2): 149–178.

Mannonen, L. (1993) Barley cell culture as a producer of heterologous protein. VTT Publications 138, Espoo (ISBN 951-38-4356-8).

Mannonen, L., Kauppinen, V. and Enari, T. M. (1994) Recent developments in the genetic engineering of barley. Crit. Rev. in Biotech. 14: 287–310.

McElroy, D., Zhang, W., Cao, J. and Wu, R. (1990) Isolation of an efficient actin promoter for use in rice transformation. Plant Cell 2: 163–171.

Merkle, S. A., Parrott, W. A. and Flinn, B. S. (1995) Morphogenic aspects of somatic embryogenesis. In In vitro Embryogenesis in Plants. Thorpe, T. A. Ed. Kluwer Academic Publishers. Dordrecht. pp. 155–203.

Murashige, T. and Skoog, F. (1962) A revised medium for rapid growth and bioassays with tobacco tissue cultures. Physiol. Plant. 15: 473–497.

Nehra, N. S., Chibbar, R. N., Leung, N., Caswell, K., Mallard, C., Steinhauer, L., Baga, M. and Kartha, K. K. (1994) Self-fertile transgenic wheat plants regenerated from isolated scutellar tissues following microprojectile bombardment with two distinct gene constructs. Plant J. 5: 285–297.

Paszkowski, J., Shillito, R. D., Saul, M. W., Mandak, V., Hohn, B. and Potrykus, I. (1984) Direct gene transfer to plants. EMBO J. 3: 2717.

Pen, J., Sijmons, P. C., Van Ooijen, A. J. J. and Hoekema, A. (1993) Protein production in transgenic crops: analysis of plant molecular farming in transgenic plant fundamentals and applications. M. Dekker. Ed. New York. pp. 239–241.

Potrykus, I. (1990) Gene transfer to cereals: an assessment. Bio/Technol. 8(6): 535–542.

Ritala, A., Aspegren, K., Kurten, U., Salmenkallio-Marttila, M., Mannonen, L., Hannus, R., Kauppinen, V., Teeri, T. H. and Enari, T. -M. (1994) Fertile transgenic barley by particle bombardment of immature embryos. Plant Mol. Biol. 24: 317–325.

Rogers, S. W. and Rogers, J. C. (1992) The importance of DNA methylation for stability of foreign DNA in barley. Plant Mol. Biol. 18:945.

Sambrook, J., Fritsch, E. F. and Maniatis, T. (1989) Molecular Cloning: A Laboratory Manual. Second ed. Cold Spring Harbor Press, New York.

Schaeffer, G. W., Lazar, M. D. and Baenziger, P. S. (1984) Chapter 5—Wheat. In Handbook of Plant Cell Culture. Vol. 2. Crop Species. Sharp, W. R., Evans, D. A., Ammirato, P. V. and Yamada, Y. Eds. Collier Macmillan Publishers. London, UK. pp. 108–136.

Schiavone F. M. and Racusen R. H., 1990. Microsurgery reveals regional capabilities for pattern reestablishment in somatic carrot embryos. Dev. Bio., 141: 211–219.

Sheveleva, E., Chmara, W., Bohnert, H. J. and Jensen, R. G. (1997) Increased salt and drought tolerance by D-ononitol production in transgenic *Nicotiana tabacum* L. Plant Physiol. 115: 1211–1219.

Spoerlein, B., Mayer, A., Dahlfeld, G. and Koop, H. U. (1991) A microassay for quantitative determination of beta-glucuronidase reporter gene activities in individually selected single higher plant cells. Plant Sci. 78(1): 73–80.

Thorpe T. A. (1993) In vitro organogenesis and somatic embryogenesis: Physiological and biochemical aspects. In Morphogenesis in Plants, Roubelakis-Angelakis K. A. and Tran Thanh Van K. (Eds). Plenum Press, New York. pp. 19–38.

Töpfer, R., Gronenborn, B., Schell, J. and Steinbiss, H. H. (1989) Improved sets of expression vectors for high level gene expression of chimaeric genes in seed derived embryos. Plant Cell 1: 133–139.

Toyoda, H., Yamaga, T., Matsuda, Y. and Ouchi, S. (1990) Transient expression of the β-glucuronidase gene introduced into barley coleoptile cells by microinjection. Plant Cell Rep. 9: 299–302.

Wan, Y. and Lemaux, P. G. (1994) Generation of large numbers of independently transformed fertile barley plants. Plant Physiol.104: 37–48.

Weeks, J. T., Anderson, O. D. and Blechl, A. E. (1993) Rapid production of multiple independent lines of fertile transgenic wheat (*Triticum aestivum*). Plant Physiol. 102: 1077–1084.

Wetherell D. F. (1979) In vitro embryoid formation in cells derived from somatic plant tissues. In: Propagation of Higher Plants Through Tissue Culture. A Bridge between Research and Application, Hughes K. W., Henke R. and Constantin M. (eds). Conf-780411, US Tech Inf Serv, Springfield, Va., pp. 102–124.

Yao, Q. A., Simion, E., William, M., Krochko, J. and Kasha, K. J. (1997) Biolistic transformation of haploid isolated microspores of barley (*Hordeum vulgare L.*). Genome 40: 570–581.

Yeung E. C. (1995) Structural and Developmental Patterns in Somatic Embryogenesis. In In vitro embryogenesis in plants, Thorpe T. A. (Ed.) Kluwer Academic Publishers, Boston. pp. 205–248.

Zrÿd, J. P. and Richards, B. (1988) Cultures de cellules, tissus et organes végétaux—Fondements theoriques et utilisations pratiques. Presses polytechniques romandes. p. 308.

PATENT LITERATURE

Adams, T. R., Chambers, S. A., Daines, R. J., Gordon-Kamm, W. J., Kausch, A. P., Lemaux, P. G., Mackey, C. J., Mangano, M. L., O'Brien, J. V., Rice, T. B., Spencer, T. M., Start, W. G. and Willetts, N. G. Methods and compositions for the production of stably transformed fertile monocot plants and cells thereof. U.S. Pat. No. 5,874,265, issued Feb. 23, 1999.

Chang, Y., Wong, J. R., Itano, A., Mejza, S. J. and Walker, L. Methods for stable transformation of wheat. U.S. Pat. No. 5,610,042, issued Mar. 11, 1997.

Cheng, D. S. K. Process for regenerating cereals. U.S. Pat. No. 4,666,844, issued May 19, 1997.

D'Halluin, K. and Gobel, E. Process for transforming monocotyledonous plants. U.S. Pat. No. 5,641,664, issued Jun. 24, 1997.

D'Halluin, K. and Gobel, E. Process for transforming monocotyledonous plants. U.S. Pat. No. 5,712,135, issued Jan. 27, 1998.

Dudits, D., Morocz, S. and Nemeth, J. *Zea Mays* (L.) With capability of long term, highly efficient plant regeneration including fertile transgenic maize plants having a heterologous gene, and their preparation. U.S. Pat. No. 5,792,936, issued Aug. 11, 1998.

Frenkel, C., Chin, C. and Havkin-Frenkel, D. Method for stimulating cell multiplication, differentiation, embryogenesis, and respiration in plant cell tissue culture by the addition of a glycoprotein extensin to culture medium. U.S. Pat. No. 5,409,828, issued Apr. 25, 1995.

Fry, J. E. and Zhou, H. Rapid and efficient regeneration of transgenic plants. U.S. Pat. No. 5,631,152, issued May 20, 1997.

Genovesi, A. D. and Yingling, R. A. Isolated microspore and anther culture of corn. U.S. Pat. No. 5,322,789, issued Jun. 21, 1994.

Genovesi, A. D. and Yingling, R. A. Isolated microscope and anther culture of maize. U.S. Pat. No. 5,445,961, issued Aug. 29, 1995.

Nehra, N. S., Kartha, K. K. and Chibbar, R. N. Enhanced regeneration system. U.S. Pat. No. 5,589,617, issued Dec. 31, 1996.

Rikiishi, K., Noda, K. and Kihara, M. A method of producing transformed cells of barley. International Publication No. WO 99/04618, published Feb. 4, 1999.

Stuart, D. A. and Strickland, S. G. Methods and media for enhanced somatic embryogenesis. Canadian Patent No. 1,292,959, issued Dec. 10, 1991.

Wu, R. J. and Ho, T. D. Production of water stress or salt stress tolerant transgenic cereal plants. U.S. Pat. No. 5,981,842, issued Nov. 9, 1999.

All publications mentioned in this specification are indicative of the level of skill in the art to which this invention pertains. To the extent they are consistent herewith, all publications mentioned in this specification are herein incorporated by reference to the same extent as if each individual publication was specifically and individually indicated to be incorporated by reference. No admission is made that any cited reference constitutes prior art.

Although the foregoing invention has been described in some detail by way of illustration and example, for purposes of clarity and understanding it will be understood that certain changes and modifications may be made without departing from the scope or spirit of the invention as defined by the following claims.

What is claimed is:

1. A process for inducing direct somatic embryogenesis in Pooideae and rapidly regenerating fertile plants, comprising the steps of:
   a) culturing isolated immature scutella cells of Pooideae in or on a culture medium comprising auxin, cytokinin and polyamine in amounts effective to cause direct formation of primary embryos without an intervening callus stage, at least until at least one primary embryo reaches the globular developmental stage, the auxin being present in greater proportion than the cytokinin; and one of the following steps selected from:
   b) culturing one or more of the primary embryos from step (a) under conditions conducive to regeneration of plantlets from the primary embryos, and culturing the primary embryo in or on a regeneration medium; or
   c) culturing one or more of the primary embryos at the globular developmental stage and no longer than the coleoptilar stage from step (a) in or on a culture medium comprising auxin, cytokinin, and polyamine in amounts effective to cause induction of secondary embryo formation, at least until secondary embryogenesis is detected, the cytokinin beina present in greater proportion than the auxin, and culturing one or more of the secondary embryos under conditions conducive to regeneration of plantlets from the secondary embryos.

2. The process of claim 1, wherein, in step (a), the ratio of auxin to cytokinin in the culture medium is from about 5 $\mu$M auxin per 1 $\mu$M cytokinin to about 20 $\mu$M auxin per 1 $\mu$M cytokinin.

3. The process of claim 2, wherein, in step (a) the culture medium includes the plant growth regulators:
   i) from about 15 $\mu$M auxin to about 45 $\mu$M auxin;
   ii) from about 15 $\mu$M polyamine to about 45 $\mu$M polyamine; and
   iii) from about 1 $\mu$M cytokinin to about 5 $\mu$M cytokinin.

4. The process of claim 1, wherein, in step (a), the ratio of auxin to cytokinin in the culture medium is about 14 $\mu$M auxin per 1 $\mu$M cytokinin.

5. The process of claim 4, wherein, in step (a), the culture medium includes the plant growth regulators of:
   i) about 30 $\mu$M auxin;
   ii) about 30 $\mu$M polyamine; and
   iii) about 2 $\mu$M cytokinin.

6. The process of claim 1, wherein, in step (a), the culture medium is DSEM medium.

7. The process of claim 3, wherein steps (a) and (b) are conducted, and the regeneration medium is MS medium.

8. The process of claim 7, further comprising, before step (b), the step of culturing the primary embryo under conditions conducive to germination of the primary embryos until germination of at least one of the primary embryos commences.

9. The process of claim 8, wherein the germination step comprises culturing the primary embryo in or on a culture medium which comprises polyamine in an amount effective to cause germination of the primary embryos, and which is essentially free of either auxin or cytokinin.

10. The process of claim 9, wherein the culture medium comprises from about 15 $\mu$M polyamine to about 45 $\mu$M polyamine.

11. The process of claim 9, wherein the culture medium comprises about 30 $\mu$M polyamine.

12. The process of claim 9, wherein the germination step comprises culturing the primary embryo in or on GEM medium.

13. The process of claim 7, further comprising the step of culturing the plantlets under conditions conducive to induction of root formation until the plantlets form roots.

14. The process of claim 13, further comprising the step of transplanting the plantlets to soil and growing them to maturity.

15. The process of claim 14, wherein the scutella cells are selected from the genera consisting of *Triticum, Hordeum, Secale, Avena, Dactylis*, and *Bromus*.

16. The process of claim 15, wherein the scutella cells are selected from the group consisting of *Triticum durum* amphiploids, *Hordeum vulgare, Triticum aestivum, Triticum durum, Triticum monococum, Triticum urartu, Secale cereale*, and *Avena sativa* scutella cells.

17. The process of claim 15, wherein the scutella cells of step (a) are free of a germ.

18. The process of claim 17, which further includes, after step (a), cutting the scutellum carrying the primary embryo into a plurality of pieces prior to culturing in step (b).

19. The process of claim 18, wherein the scutellum carrying the primary embryo is cut into two to four pieces.

20. The process of claim 15, wherein step (a) further comprises the step of introducing foreign DNA into the scutella cells or primary embryo so that the foreign DNA becomes stably integrated into the genome of the cells.

21. The process of claim 20, wherein the foreign DNA is introduced into the scutella cells or primary embryo by particle bombardment or by *Agrobacterium*-mediated transformation.

22. The process of claim 21, wherein the foreign DNA is introduced into the scutella cells or primary embryo in step (a) during the development of the primary embryo.

23. The process of claim 22, wherein the foreign DNA is introduced into the scutella cells between zero to five days after commencement of tissue culture.

24. The process of claim 22, wherein the foreign DNA is introduced into the scutella cells or the primary embryo after two days following commencement of tissue culture.

25. The process of claim 22, wherein after the foreign DNA has been introduced, the scutella cells or primary embryo are transferred to a media for steps (a) and (b) which includes a selective agent to identify a transformed plant cell that has incorporated the foreign DNA.

26. The process of claim 25, wherein the transformed plant cell is cultured in media to support regeneration of transformants.

27. The process of claim 26, which further comprises confirming expression of the foreign DNA in the transformants by one or both of polymerase chain reaction and Southern blot analyses.

28. The process of claim 3, wherein, in step (c), the ratio of auxin to cytokinin in the culture medium is from about 0.05 $\mu$M auxin per 1 $\mu$M cytokinin to about 0.2 $\mu$M auxin per 1 $\mu$M cytokinin.

29. The process of claim 28, wherein, in step (c), the culture medium includes the plant growth regulators:
  i) from about 5 $\mu$M auxin to about 15 $\mu$M auxin;
  ii) from about 15 $\mu$M polyamine to about 45 $\mu$M polyamine; and
  iii) from about 50 $\mu$M cytokinin to about 200 $\mu$M cytokinin.

30. The process of claim 3, wherein, in step (c) the ratio of auxin to cytokinin is about 0.1 $\mu$M auxin per 1.0 $\mu$M cytokinin.

31. The process of claim 30, wherein, in step (c), the culture medium includes the plant growth regulators of:
  i) about 11 $\mu$M auxin;
  ii) about 30 $\mu$M polyamine; and
  iii) about 110 $\mu$M cytokinin.

32. The process of claim 3, wherein, in step (c), the culture medium is SEM medium.

33. The process of claim 32, wherein step (c) comprises culturing the secondary embryo in or on a regeneration medium.

34. The process of claim 33, wherein the regeneration medium is MS medium.

35. The process of claim 33, further comprising, before step (c), the step of culturing the secondary embryo under conditions conducive to germination of the secondary embryos until germination of at least one of the secondary embryos commences.

36. The process of claim 35, wherein the germination step comprises culturing the secondary embryo in or on a culture medium which comprises polyamine in an amount effective to cause germination of the secondary embryos, and which is essentially free of either auxin or cytokinin.

37. The process of claim 36, wherein the culture medium comprises from about 15 $\mu$M polyamine to about 45 $\mu$M polyamine.

38. The process of claim 36, wherein the culture medium comprises about 30 $\mu$M polyamine.

39. The process of claim 36, wherein the germination step comprises culturing the secondary embryo in or on GEM medium.

40. The process of claim 33, further comprising the step of culturing the plantlets under conditions conducive to induction of root formation until the plantlets form roots.

41. The process of claim 40, further comprising the step of transplanting the plantlets to soil and growing them to maturity.

42. The process of claim 41, wherein the scutella cells are selected from the genera consisting of *Triticum, Hordeum, Secale, Avena, Dactylis*, and *Bromus*.

43. The process of claim 42, wherein the scutella cells are selected from the group consisting of *Triticum durum* amphiploids, *Hordeum vulgare, Triticum aestivum, Triticum durum, Triticum monococum, Triticum urartu, Secale cereale*, and *Avena sativa* scutella cells.

44. The process of claim 42, wherein the scutella cells of step (a) are free of a germ.

45. The process of claim 44, which further includes, after step (a), cutting the primary embryo into a plurality of pieces before culturing in step (c).

46. The process of claim 45, wherein the primary embryo is cut into two to four pieces.

47. The process of claim 45, which further comprises, before step (c), the step of cutting the primary embryo carrying the secondary embryo into a plurality of pieces, or cutting a germinating leaf if developed, to obtain a high frequency of germination of secondary embryo.

48. The process of claim 47, wherein the primary embryos carrying the secondary embryo is cut into two pieces.

49. The process of claim 42, wherein step (a) further comprises the step of introducing foreign DNA into the scutella cells or the primary embryo so that the foreign DNA becomes stably integrated into the genome of the cells.

50. The process of claim 49, wherein the foreign DNA is introduced into the scutella cells or primary embryo by particle bombardment or by *Agrobacterium*-mediated transformation.

51. The process of claim 50, wherein the foreign DNA is introduced into the scutella cells or the primary embryo in step (a) during the development of the primary embryo.

52. The process of claim 51, wherein the foreign DNA is introduced into the scutella cells or the primary embryo between zero to five days after commencement of tissue culture.

53. The process of claim 51, wherein the foreign DNA is introduced into the scutella cells or the primary embryo after two days following commencement of tissue culture.

54. The process of claim 51, wherein after the foreign DNA has been introduced, the scutella cells or primary embryo are transferred to a media for step (c), and optionally for step (a), which includes a selective agent to identify a transformed plant cell that has incorporated the foreign DNA.

55. The process of claim 54, wherein the transformed plant cell is cultured in media to support regeneration of transformants.

56. The process of claim 55, which further comprises confirming expression of the foreign DNA in the transformants by one or both of polymerase chain reaction and Southern blot analyses.

* * * * *